(12) United States Patent
Bartlett, II et al.

(10) Patent No.: US 11,000,658 B2
(45) Date of Patent: *May 11, 2021

(54) DEVICE TO REDUCE DISCOMFORT IN THE UPPER AIRWAY

(71) Applicant: AWAIR, INC., Mountain View, CA (US)

(72) Inventors: Rush L. Bartlett, II, Mountain View, CA (US); Ivan Tzvetanov, Berkeley, CA (US); Ryan J. F. Van Wert, Palo Alto, CA (US)

(73) Assignee: AWAIR, INC., Mountain View, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 15/310,671

(22) PCT Filed: May 18, 2015

(86) PCT No.: PCT/US2015/031387
§ 371 (c)(1),
(2) Date: Nov. 11, 2016

(87) PCT Pub. No.: WO2015/179300
PCT Pub. Date: Nov. 26, 2015

(65) Prior Publication Data
US 2017/0095628 A1    Apr. 6, 2017

Related U.S. Application Data

(60) Provisional application No. 61/994,991, filed on May 18, 2014, provisional application No. 62/036,076, (Continued)

(51) Int. Cl.
*A61M 16/04* (2006.01)
*A61M 19/00* (2006.01)
*A61M 11/00* (2006.01)

(52) U.S. Cl.
CPC ........ *A61M 16/0409* (2014.02); *A61M 11/00* (2013.01); *A61M 16/049* (2014.02); (Continued)

(58) Field of Classification Search
CPC .............. A61M 16/04; A61M 16/0434; A61M 16/0463; A61M 16/0484; A61M 16/0445; (Continued)

(56) References Cited

U.S. PATENT DOCUMENTS 1,236,865 A   8/1917  Pittenger
1,856,811 A   5/1932  Inaki
(Continued)

FOREIGN PATENT DOCUMENTS

EP         0 458 550        11/1991
WO    WO 1995/008305        3/1995
(Continued)

OTHER PUBLICATIONS

Extended European Search Report dated Dec. 12, 2017 for European Application No. 15 796 981.7, 6 pages.
(Continued)

*Primary Examiner* — Margaret M Luarca
(74) *Attorney, Agent, or Firm* — Merchant & Gould P.C.

(57) ABSTRACT

A device for delivering a substance to an airway of a patient may include a laryngeal mask airway device, at least one substance delivery reservoir coupled with the laryngeal mask airway device for delivering the substance to the airway of the patient, and at least one conduit coupled with the laryngeal mask airway. The at least one conduit may have a proximal end configured to couple with a source of the substance residing outside the patient and a distal end in fluid communication with the at least one substance delivery reservoir.

10 Claims, 25 Drawing Sheets

Related U.S. Application Data filed on Aug. 11, 2014, provisional application No. 62/036,091, filed on Aug. 11, 2014.

(52) U.S. Cl.
CPC .... *A61M 16/0434* (2013.01); *A61M 16/0436* (2014.02); *A61M 16/0463* (2013.01); *A61M 16/0479* (2014.02); *A61M 16/0481* (2014.02); *A61M 16/0484* (2014.02); *A61M 16/0486* (2014.02); *A61M 19/00* (2013.01)

(58) Field of Classification Search
CPC .......... A61M 16/0479; A61M 16/0481; A61M 16/0461; A61M 16/0477; A61M 2025/0057; A61M 16/0402
See application file for complete search history.

(56) References Cited

U.S. PATENT DOCUMENTS

| | | | |
|---|---|---|---|
| 3,814,103 | A | 6/1974 | Fettel et al. |
| 4,072,153 | A | 2/1978 | Swartz |
| 4,182,326 | A | 1/1980 | Ogle |
| 4,309,994 | A | 1/1982 | Grunwald |
| 4,644,947 | A | 2/1987 | Whitwam et al. |
| 4,693,243 | A | 9/1987 | Buras |
| 5,146,916 | A | 9/1992 | Catalani |
| 5,313,939 | A | 5/1994 | Gonzalez |
| 5,389,074 | A | 2/1995 | Parker et al. |
| 5,523,092 | A | 6/1996 | Hanson et al. |
| 5,699,787 | A | 12/1997 | Thompson |
| 5,707,352 | A | 1/1998 | Sekins et al. |
| 5,709,874 | A | 1/1998 | Hanson et al. |
| 5,803,078 | A | 9/1998 | Brauner |
| 5,819,723 | A | 10/1998 | Joseph |
| 5,891,101 | A | 4/1999 | Wilcox et al. |
| 5,964,223 | A | 10/1999 | Baran |
| 5,985,307 | A | 11/1999 | Hanson et al. |
| 6,402,735 | B1 | 6/2002 | Langevin |
| 6,487,446 | B1 | 11/2002 | Hill et al. |
| 6,526,976 | B1 | 3/2003 | Baran |
| 6,551,290 | B1 | 4/2003 | Elsberry et al. |
| 6,729,334 | B1 | 5/2004 | Baran |
| 6,766,801 | B1 | 7/2004 | Wright |
| 7,153,292 | B2 | 12/2006 | Morris et al. |
| 7,360,541 | B2 | 4/2008 | Dhuper et al. |
| 7,469,700 | B2 | 12/2008 | Baran |
| 7,766,961 | B2 | 8/2010 | Patel et al. |
| 8,074,649 | B2 | 12/2011 | Dhuper et al. |
| 8,424,516 | B2 | 4/2013 | Gray et al. |
| 8,500,939 | B2 | 8/2013 | Nimkar et al. |
| 8,556,880 | B2 | 10/2013 | Freyman et al. |
| 8,777,927 | B2 | 7/2014 | Cheney |
| 8,944,709 | B2 | 2/2015 | Ellsworth et al. |
| 9,409,003 | B2 | 8/2016 | Bartlett, II et al. |
| 9,744,340 | B2 | 8/2017 | Bartlett, II et al. |
| 10,363,403 | B2 | 7/2019 | Bartlett, II et al. |
| 2001/0050082 | A1 | 12/2001 | Christopher |
| 2003/0101991 | A1 | 6/2003 | Trueba |
| 2004/0236286 | A1 | 11/2004 | Klein |
| 2005/0016542 | A1 | 1/2005 | Wright |
| 2006/0106350 | A1 | 5/2006 | Spitz |
| 2006/0162730 | A1 | 7/2006 | Glassenberg et al. |
| 2009/0112047 | A1 | 4/2009 | Carol et al. |
| 2009/0187238 | A1 | 7/2009 | Weber et al. |
| 2009/0235935 | A1 | 9/2009 | Pacey |
| 2009/0240199 | A1 | 9/2009 | Rahimsobhani |
| 2009/0260632 | A1 | 10/2009 | Abnousi et al. |
| 2010/0089393 | A1 | 4/2010 | Brain |
| 2010/0179511 | A1 | 7/2010 | Rajan et al. |
| 2011/0023871 | A1 | 2/2011 | Pacey |
| 2011/0030680 | A1 | 2/2011 | Wood et al. |
| 2011/0109458 | A1 | 5/2011 | Shipman |
| 2012/0184921 | A1 | 7/2012 | Brillant |
| 2013/0053636 | A1 | 2/2013 | Hayman et al. |
| 2014/0137867 | A1 | 5/2014 | Pacey |
| 2014/0311497 | A1 | 10/2014 | Daly et al. |
| 2015/0122834 | A1 | 5/2015 | Ellsworth et al. |
| 2019/0344059 | A1 | 11/2019 | Bartlett et al. |

FOREIGN PATENT DOCUMENTS

| | | |
|---|---|---|
| WO | WO 2004/101028 | 11/2004 |
| WO | WO 2012/032290 | 3/2012 |
| WO | WO 2013/138861 A1 | 9/2013 |
| WO | WO 2015/038870 | 3/2015 |

OTHER PUBLICATIONS

Moyers, G., "Use of the Cook Airware Exchange Catheter in 'Bridging' the Potentially Difficult Extubation: A Case Report," AANA Journal, Aug. 2012, vol. 70, No. 4, pp. 275-278.

Rule 71(3) EPC Communication, dated Jan. 25, 2019, Intention to Grant, for application No. 15 796 981.7, 7 pp.

Rule 71(3) EPC Communication, dated Jan. 25, 2019, for application No. 15 796 981.7, text proposed for grant, 63 pp.

Extended European Search Report for EP Application No. 13 859 645.7, dated Aug. 4, 2016, 5 pp.

International Preliminary Report on Patentability for PCT/US2013/073724, dated May 12, 2014, 5 pp.

Written Opinion of the International Searching Authority for PCT/US2013/073724, dated Mar. 20, 2014, 5 pp.

International Search Report for PCT/US2013/073724, dated Mar. 20, 2014, 3 pp.

Berra, L., et al., "A Clinical Assessment of the Mucus Shaver, A Device to Keep the Endotracheal Tube Free from Secretions", Crit Care Med Jan. 2012, 40(1):119-124, 16 pp.

Chadha, N., et al., "Automated Cuff Pressure Modulation: A Novel Device to Reduce Endotracheal Tube Injury", Arch Otolaryngol Head Neck Surg/vol. 137 (No. 1), Jan. 2011, pp. 30-34, 5 pp.

Elganzouri, A.R., et al, "The Use of AIR-Q as Conduit for Fiberoptic Endotracheal Intubation in Adult Paralyzed Patients", Egyptian Journal of Anaesthesia, vol. 28, Issue 4, Oct. 2012, pp. 249-255, 7 pp.

Mallick, A., et al., "Local Anaesthesia to the Airway Reduces Sedation Requirements in Patients Undergoing Artificial Ventilation", British Journal of Anaesthesia 1996, 77, pp. 731-734, 4 pp.

Moyers, G., "Use of the Cook Airware Exchange Catheter in Bridging the Potentially Difficult Extubatioin: A Case Report", AANA.

International Preliminary Report on Patentability for PCT/US2015/031387, dated Nov. 22, 2016, 8 pp.

Extended European Search Report for Application No. 19151790.3, dated Oct. 18, 2019, 6 pages.

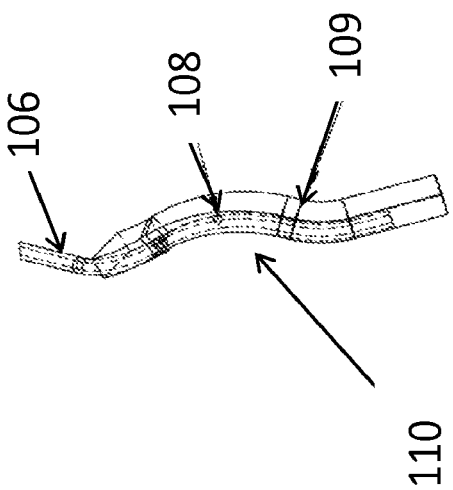
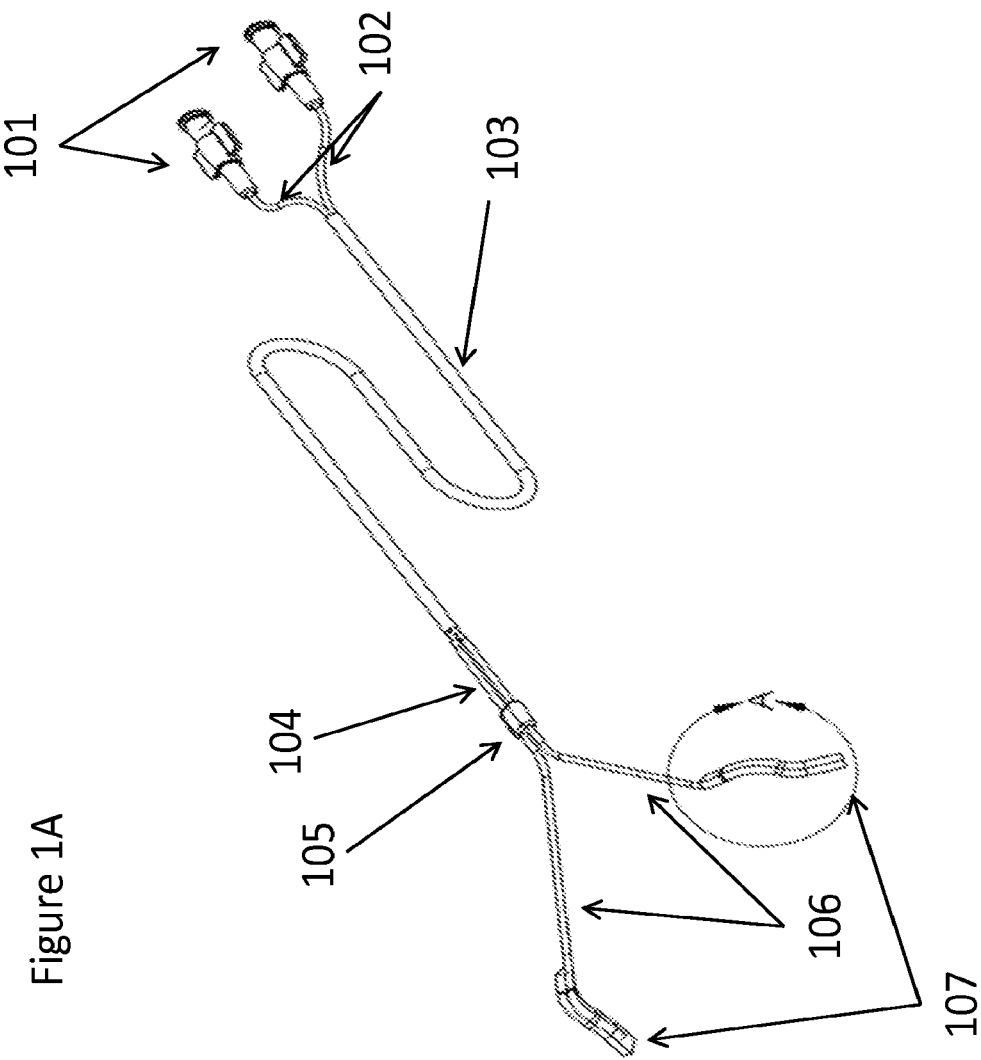
Figure 1B
Figure 1A

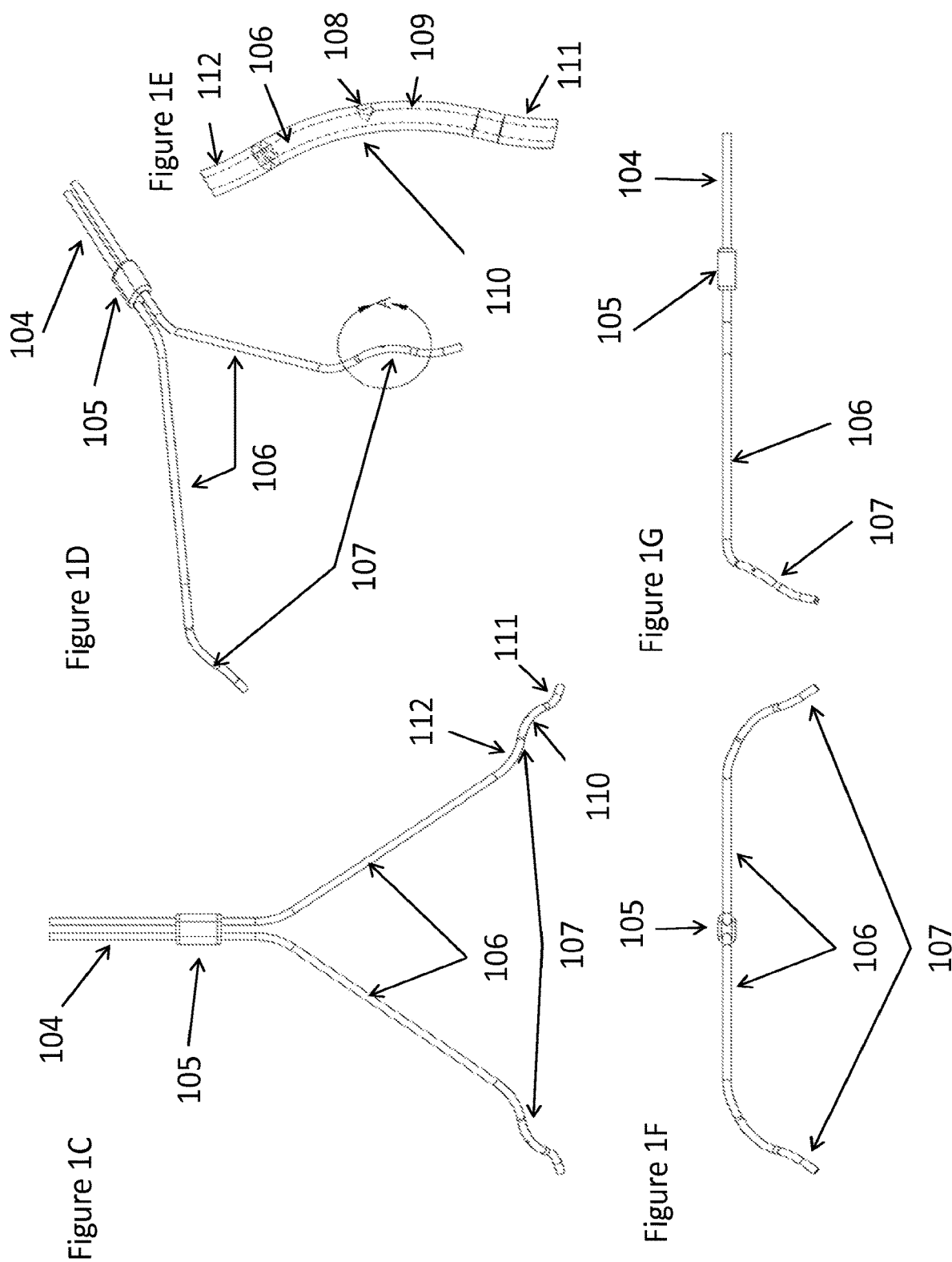

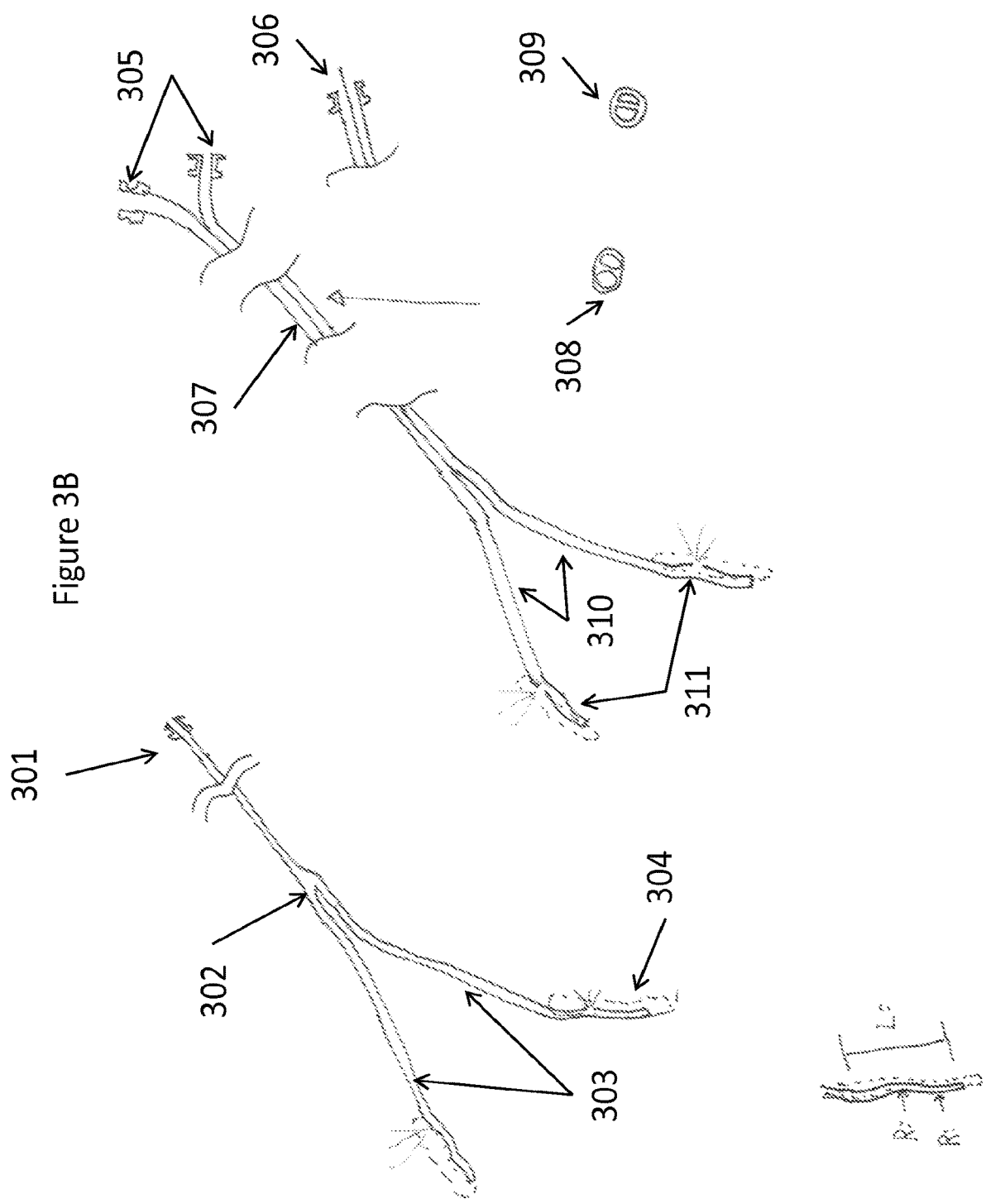

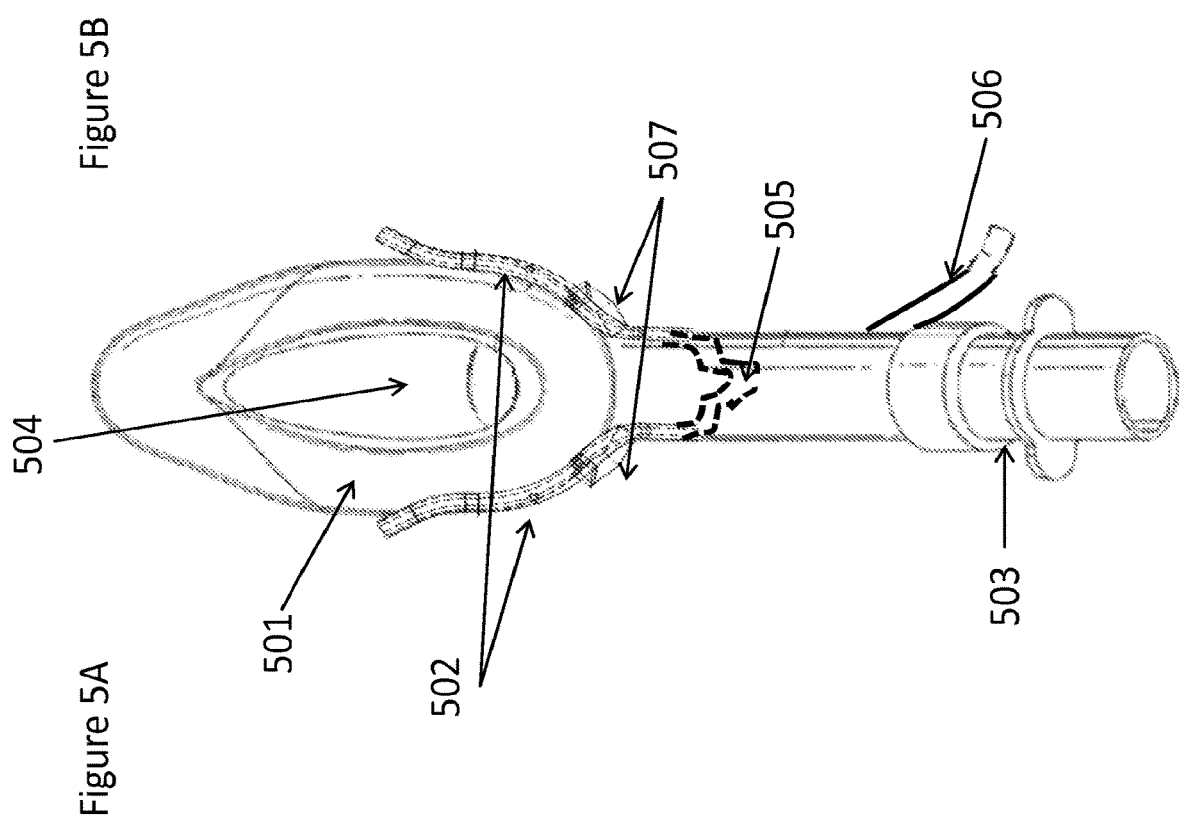

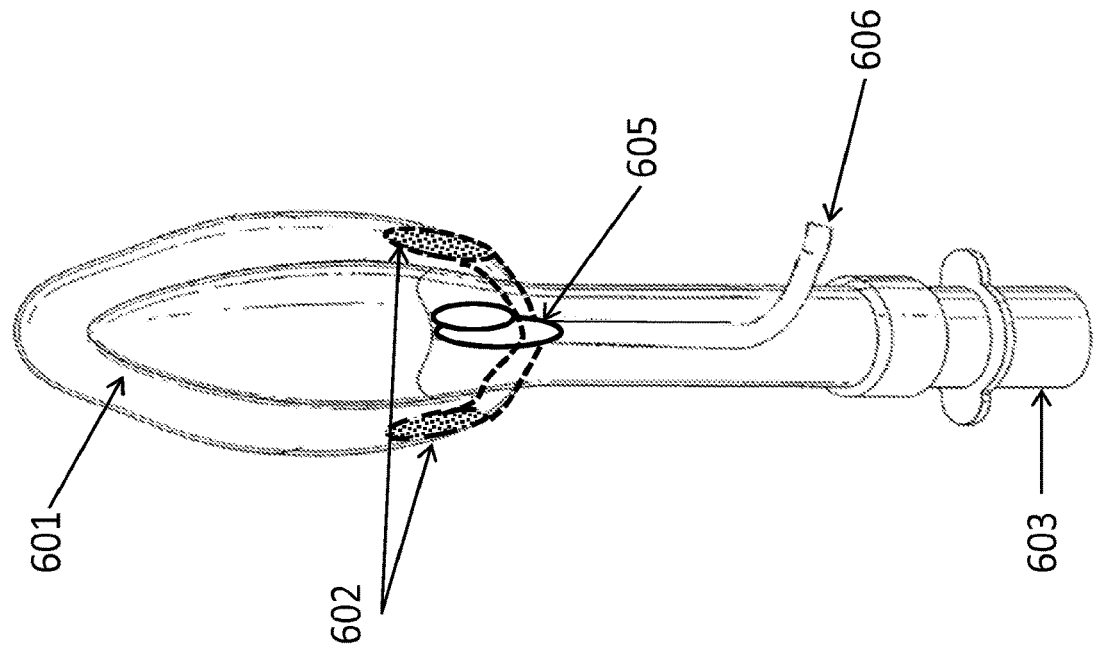
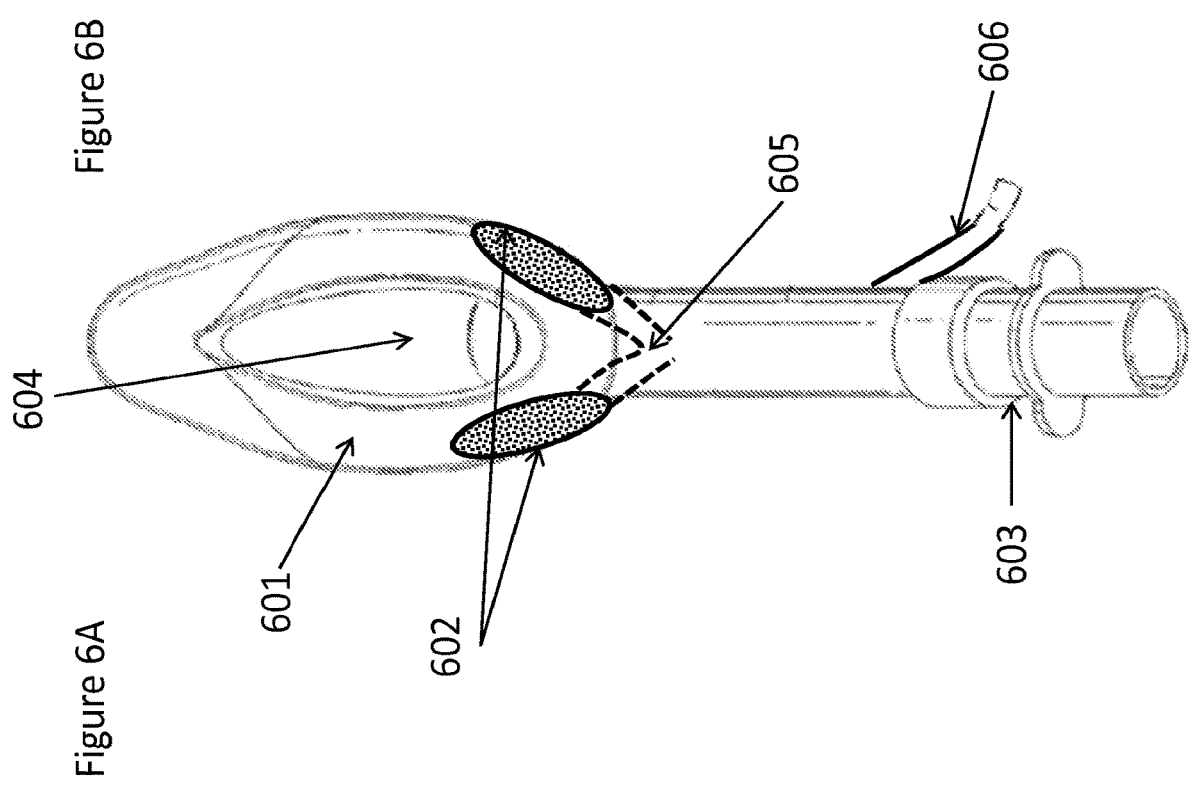
Figure 6A
Figure 6B

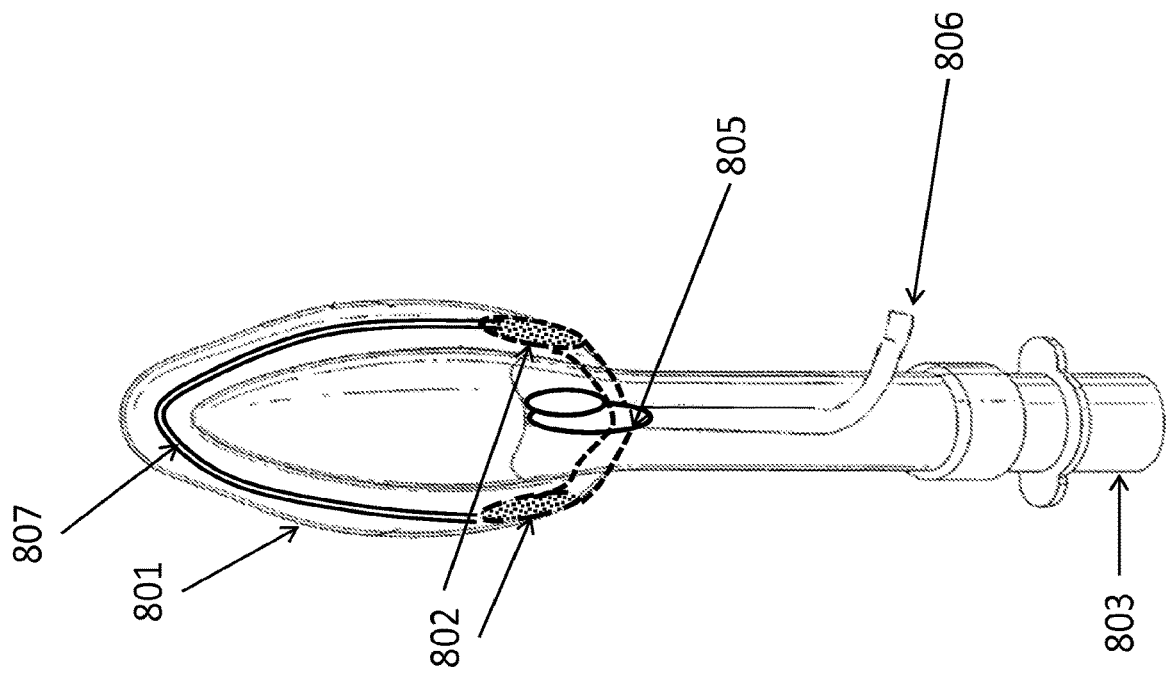
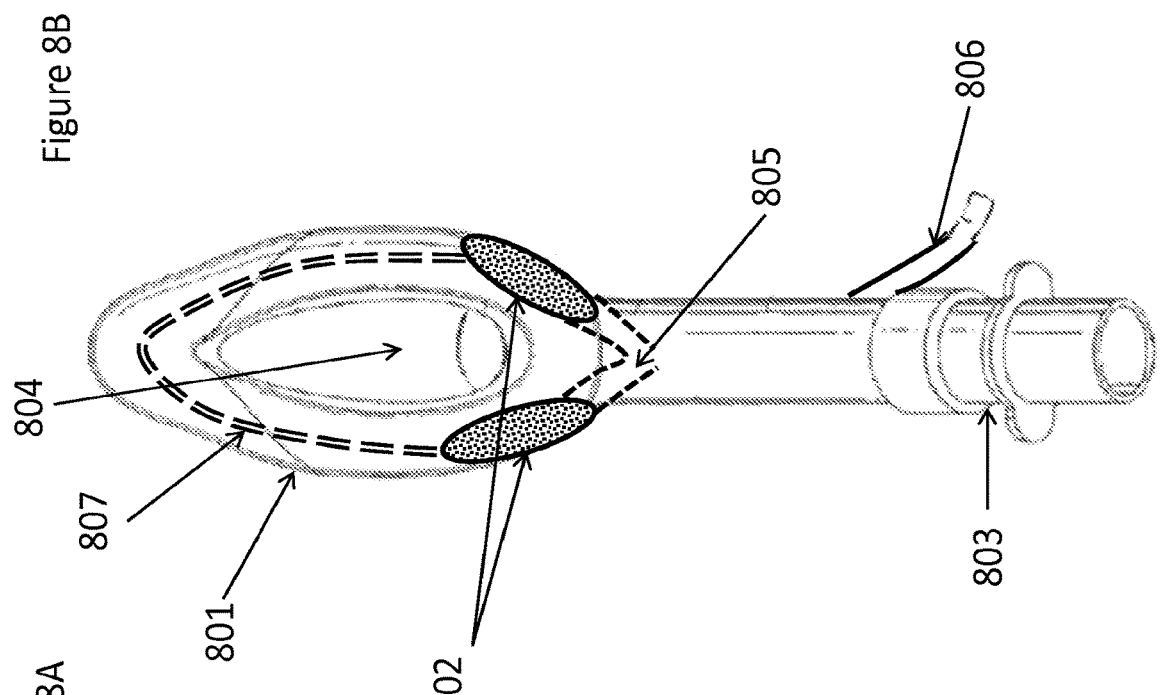
Figure 8A
Figure 8B

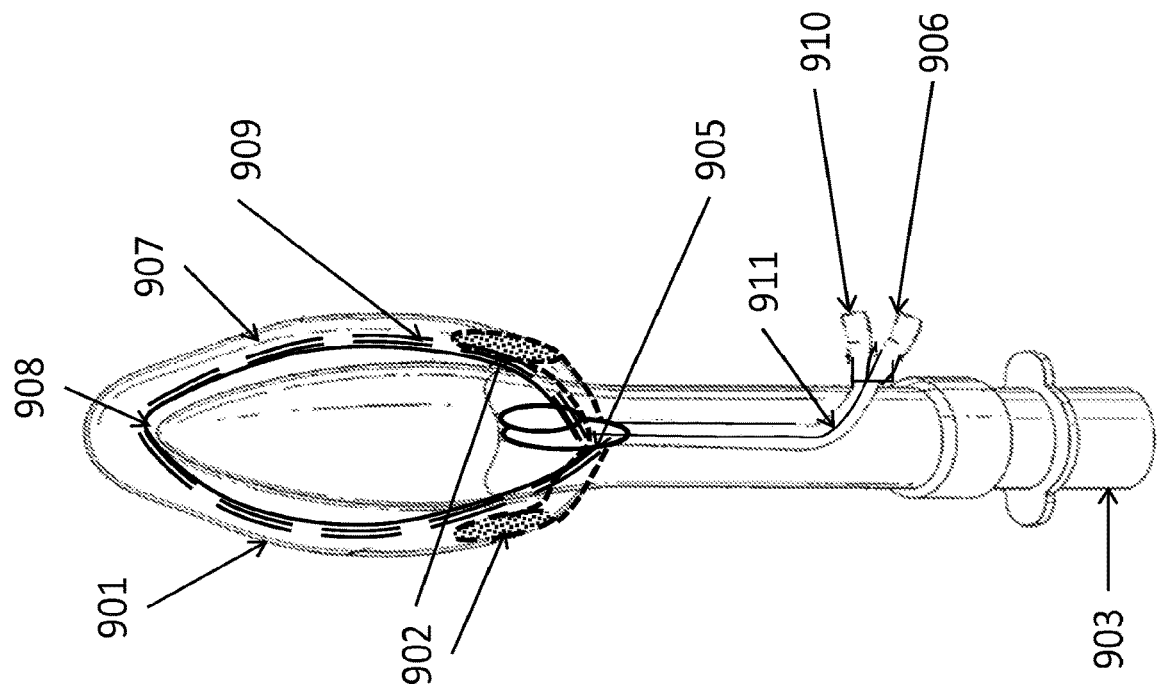
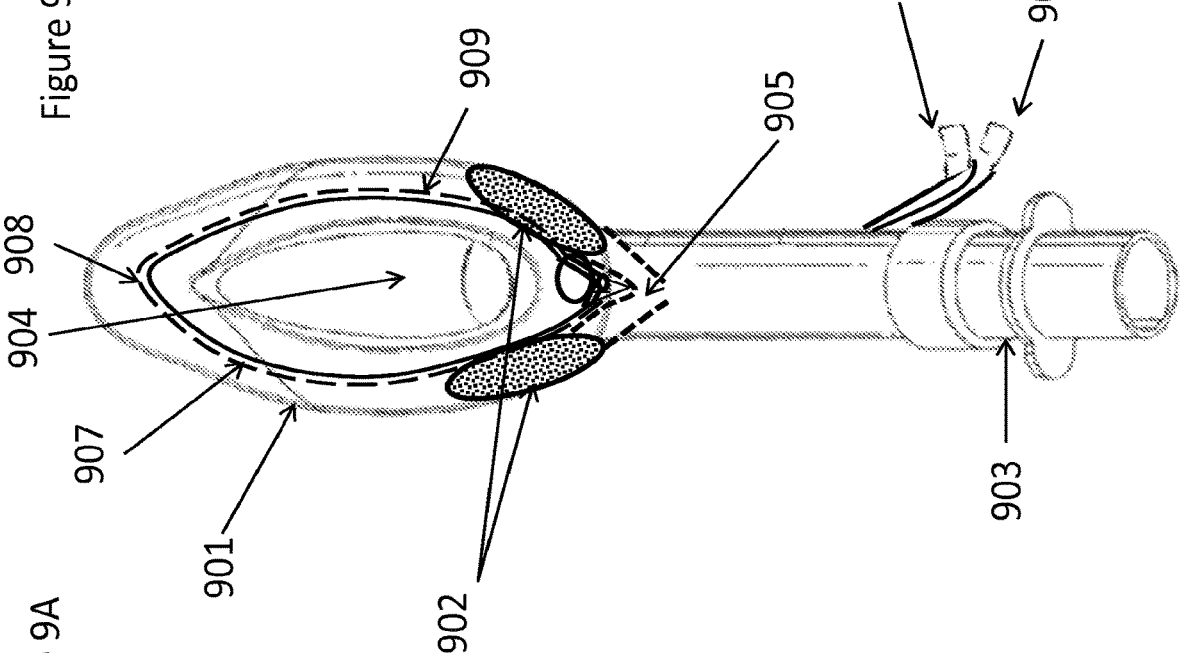

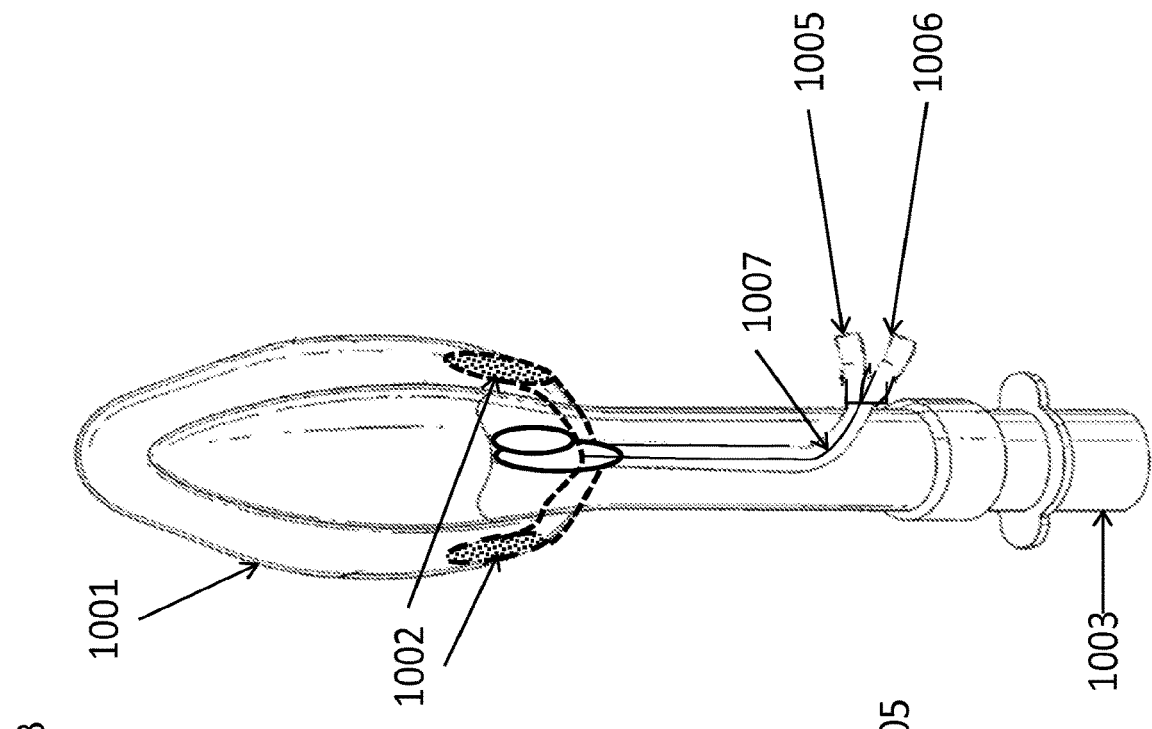
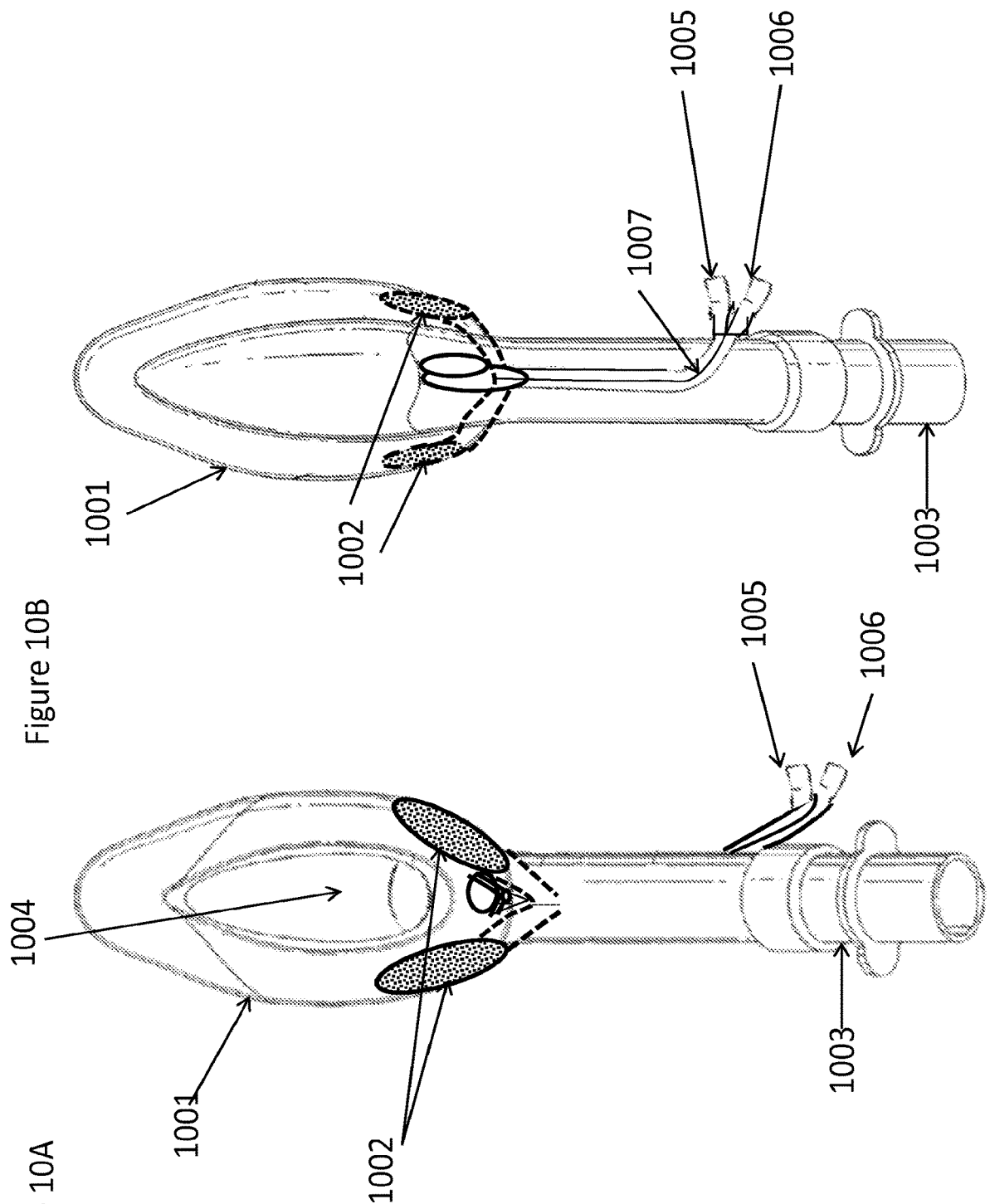

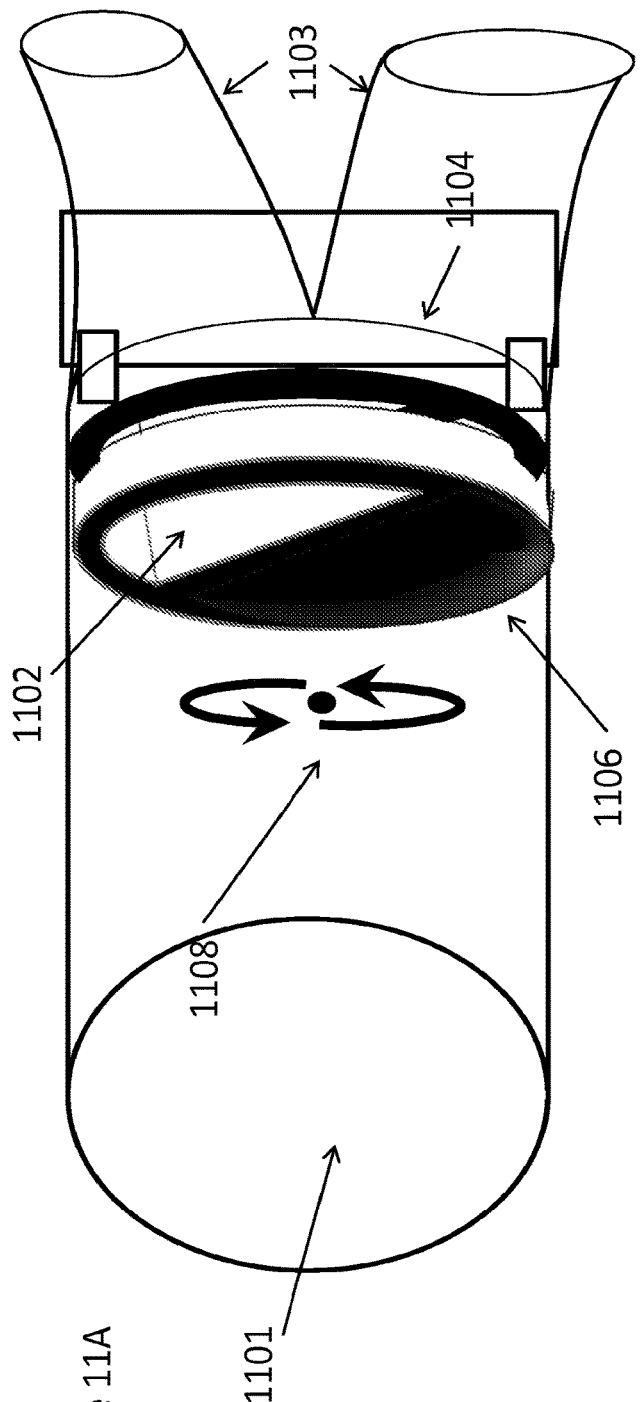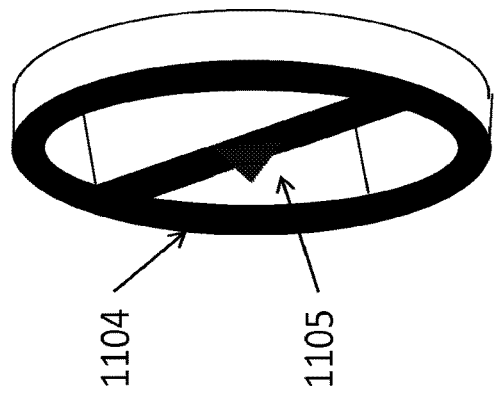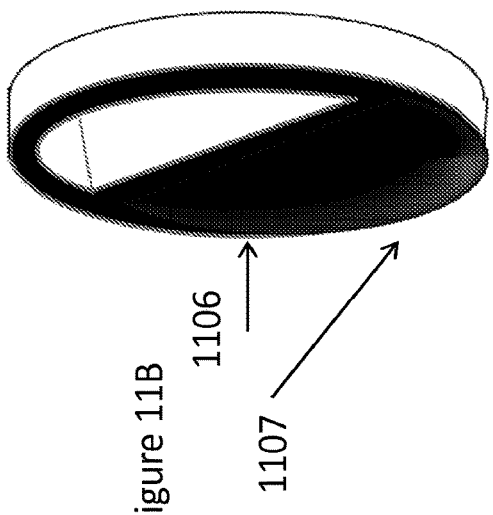
Figure 11A
Figure 11B
Figure 11C

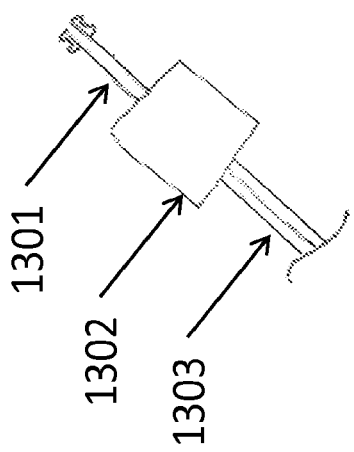
Figure 13. A
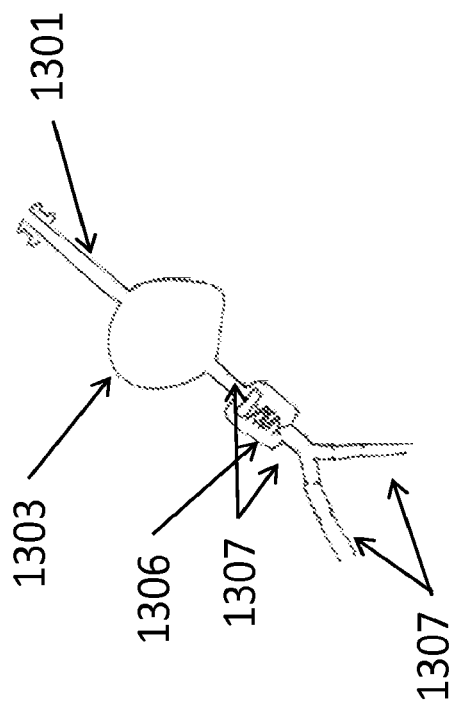
Figure 13. B

DEVICE TO REDUCE DISCOMFORT IN THE UPPER AIRWAY

CROSS-REFERENCE TO RELATED APPLICATION(S)

This application is a U.S. national stage application of PCT Application No. PCT/US2015/031387, filed on May 18, 2015, which claimed priority from U.S. Provisional Application No. 61/994,991, entitled "Device to Reduce Discomfort in the Upper Airway," filed May 18, 2014, U.S. Provisional Patent Application No. 62/036,076, entitled "Device to Deliver Material to the Upper Airway," filed on Aug. 11, 2014 and U.S. Provisional Patent Application No. 62/036,091, entitled "Device to Deliver Material to the Upper Airway," filed on Aug. 11, 2014. The full disclosures of the above-listed patent applications are hereby incorporated by reference herein.

BACKGROUND

Pain, agitation, gagging, and other unpleasant sensations accompany many types of medical procedures, interventions and conditions in the mouth, nose, upper airway and gastrointestinal tract. Traditionally, there are few options to reduce unpleasant sensations of a foreign object, injury, or other medical condition of the upper airway, oral area, nasal area, or upper gastro-intestinal tract areas. Some traditional options to reduce this unpleasantness include injected nerve block with a needle, a onetime manual spray of local anesthetic, and the use of whole body intravenous sedation. These techniques are often inadequate or ineffective at reducing the sensations, cause side effects, only work very temporarily, or some combination thereof.

Therefore, it would be very desirable to have an improved system and method that could reduce or eliminate unpleasant sensations of a foreign object, injury, or other medical condition or procedure in the upper airway, oral area, nasal area, or upper gastro-intestinal tract. Ideally, such a system and method could be used over a prolonged period of time, with minimal side effects. It would also be ideal if such a system and method worked locally, so that general anesthesia or systemic medications were not necessary. At least some of these objectives will be met by the embodiments described herein.

BRIEF SUMMARY

Described herein is a system to modulate, reduce, or augment motor, sensory or autonomic function or perception thereof due to unpleasant sensation of a foreign object, injury, or other medical condition or procedure of the upper airway, oral area, nasal area, or upper gastro-intestinal tract.

In one aspect, a device for delivering a substance to an airway of a patient may include: a laryngeal mask airway device; at least one substance delivery reservoir coupled with the laryngeal mask airway device for delivering the substance to the airway of the patient; and at least one conduit coupled with the laryngeal mask airway. The conduit has a proximal end configured to couple with a source of the substance residing outside the patient and a distal end in fluid communication with the at least one substance delivery reservoir.

In some embodiments, the device includes at least two reservoirs disposed around a cuff of the laryngeal mask airway, and the reservoirs include multiple micropores through which the substance flows out of the laryngeal mask airway to contact the airway of the patient. In some embodiments, the device includes at least two applicators disposed around a cuff of the laryngeal mask airway, and the at least two applicators are configured to be located in contact with or near the airway of the patient when the laryngeal mask airway is disposed in the airway of the patient. In some embodiments, a wall of the laryngeal mask airway is semi-porous, to allow the substance to pass from the at least one substance delivery reservoir through the wall of the laryngeal mask airway. In various alternative embodiments, the reservoir may include, but is not limited to, a sponge, a semi-porous balloon, a balloon with micropores, an aerosol and/or a cavity formed inside the laryngeal mask airway. In some embodiments, the conduit may be a branching conduit that branches from a single proximal end to two separate distal ends. In some embodiments, the device includes two conduits attached to one another along a portion of their lengths. In various alternative embodiments, the conduit is configured to deliver the substance to at least one of an upper airway, an oral cavity, a nasal cavity, an upper gastrointestinal tract, an esophagus, a tongue, an epiglottis, tonsillar pillars, a piriform sinus, behind vocal cords, in front of vocal cords, a trachea, lungs, and/or a stomach.

In another aspect, a method for delivering a substance to an airway of a patient may involve advancing a laryngeal mask airway into the airway of the patient, connecting a proximal end of at least one conduit coupled with the laryngeal mask airway to a source of the substance, allowing the substance to pass from the source through the at least one conduit to at least one reservoir coupled with the a distal end of the at least one conduit and also coupled with the laryngeal mask airway, and delivering the substance to the airway of the patient by allowing the substance to pass out of the reservoir(s). In some embodiments, for example, the proximal end is connected with a source of an anesthetic substance.

In some embodiments, the connecting step involves connecting a single proximal end of the at least one conduit with the source of the substance, and the single proximal end branches into two distal ends to pass the substance to two reservoirs. In some embodiments, delivering the substance involves allowing the substance to pass through multiple micropores in the reservoir(s). In some embodiments, delivering the substance involves allowing the substance to pass through a semi-porous surface of the laryngeal mask airway. In some embodiments, delivering the substance involves delivering it through at least two reservoirs coupled with the laryngeal mask airway. Optionally, delivering the substance may further involve guiding the substance along a surface of the airway of the patient via at least one surface structure on an outer surface of the laryngeal mask airway. In various alternative embodiments, delivering the substance may involve delivering the substance to at least one area, such as but not limited to an upper airway, an oral cavity, a nasal cavity, an upper gastrointestinal tract, an esophagus, a tongue, an epiglottis, tonsillar pillars, a piriform sinus, behind vocal cords, in front of vocal cords, a trachea, lungs, and/or a stomach.

In another aspect, a method for delivering a substance to an airway of a patient may involve advancing a medical device into the airway of the patient to perform a function in the airway or in a gastrointestinal tract of the patient, attaching a substance delivery device to the medical device so that the substance delivery device is positioned in the airway, and delivering the substance to the airway using the substance delivery device. In various embodiments, the substance delivery device may be either a nebulizer or a sprayer. In various embodiments, the medical device may be, but is not limited to, a bronchoscope, a laryngoscope, an endotracheal tube, an endoscope, a nasogastric tube, an orogastric tube, a laryngeal airway mask, or a tracheostomy tube. In some embodiments, the medical device is an endotracheal tube, and the substance delivery device is attached to it proximal to a cuff on the endotracheal tube so that the substance is delivered to an upper portion of the airway. In other embodiments, the medical device is an endotracheal tube, and the substance delivery device comprises a nebulizer configured as a mouthpiece that surrounds the endotracheal tube.

In some embodiments, the advancing step is performed through the patient's mouth. In other embodiments, the advancing step is performed through at least one of the patient's nostrils. In such embodiments, the method may optionally also include placing a nose plug in one or both of the patient's nostrils before the advancing step, where the medical device is advanced through the nose plug. In some embodiments, the substance delivery device is attached to the medical device outside the patient, and the method further involves advancing the substance delivery device along the medical device to position the substance delivery device in the airway. In some embodiments, the attaching step is performed before the advancing step.

In another aspect, a device for delivering a substance to an airway of a patient may include: a proximal conduit portion having a first lumen; a distal conduit portion having a second and a third lumen that branch off of the first lumen of the proximal conduit portion; and a flow restriction member disposed in the proximal conduit portion that slows flow of the substance from a first flow rate proximal to the flow restriction member to a second, slower flow rate distal to the flow restriction member. In some embodiments, an inner diameter of the proximal conduit portion is between 0.02 inches and 0.15 inches. In some embodiments, the flow restriction member includes at least one opening for allowing the substance to pass through the flow restriction member, and a diameter of the at least one opening is between 0.005 inches and 0.035 inches. In various embodiments, the flow restriction member may include one or more orifice plates, restriction points, choke points, weep holes, right angles, and/or kinks in the proximal conduit portion. In some embodiments, the flow restriction member is adjustable to thereby adjust a difference between the first and second flow rates.

These and other aspects and embodiments will be described in further detail below, in reference to the attached drawing figures.

BRIEF DESCRIPTION OF DRAWINGS

FIGS. 1A-1G are various views of a catheter device with connectors, conduits, and applicators to deliver a flowing material to the upper airway, according to one embodiment;

FIGS. 3A-D are perspective views of a device and system with at least one connector connecting at least one reservoir to at least one conduit with at least one flow channel in the conduit to facilitate the flow of material to at least two other connectors and conduits or applicators for application of the material to a part of the body, according to one embodiment;

FIGS. 5A and 5B are bottom and top views, respectively, of a device configured to be used clipped to or inserted with a laryngeal mask airway (LMA) for delivery of material to the upper airway external to the lungs, according to one embodiment;

FIGS. 6A and 6B are bottom and top views, respectively, of a device configured to be physically incorporated into the structure of an LMA for the delivery of materials to the upper airway, according to one embodiment;

FIGS. 8A and 8B are bottom and top views, respectively, of a device configured to be physically incorporated into the structure of an LMA for the delivery of materials to the upper airway, according to one embodiment that contains a looped flow path to help facilitate a more even flow at the flow-splitting bifurcation;

FIGS. 9A and B are bottom and top views, respectively, of a device configured to be physically incorporated into the structure of an LMA for the delivery of materials to the upper airway and/or a capability to suction liquid from the tip or other section of the LMA through an inbuilt suction channel and port within the wall of the LMA, according to one embodiment;

FIGS. 10A and 10B are bottom and top views, respectively, of a device configured to be physically incorporated into the structure of an LMA for the delivery of materials to the airway with dual inlet ports to direct flow to two delivery applicators on either side of the LMA, according to one embodiment;

FIGS. 11A-11C are side/perspective views of a device having a flow-splitting valve that has a component that has a fin that drives rotation of the component (FIG. 11B) in a fluid flow to allow for flow to oscillate between two flow outlets FIG. 11C, according to one embodiment;

Figure 18B:
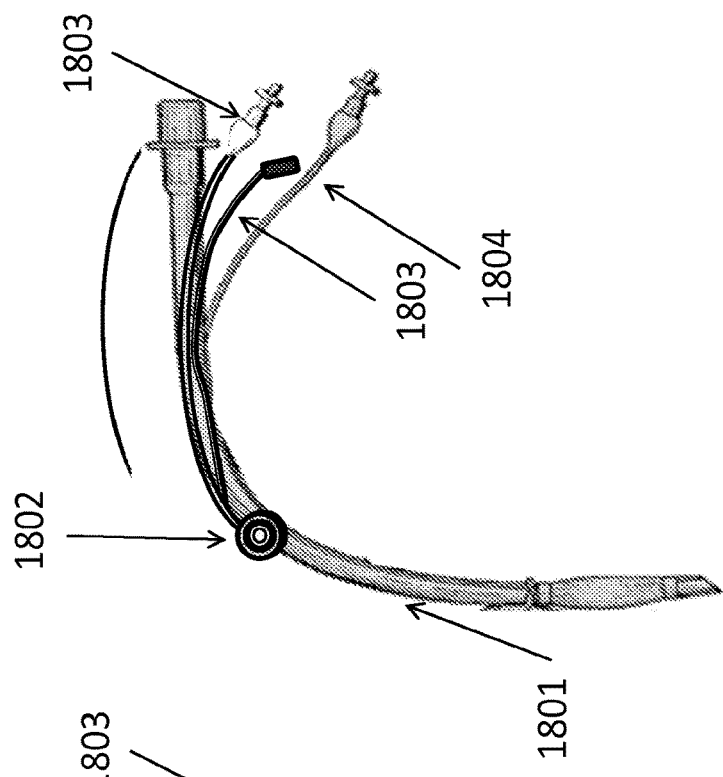
Figure 18A:
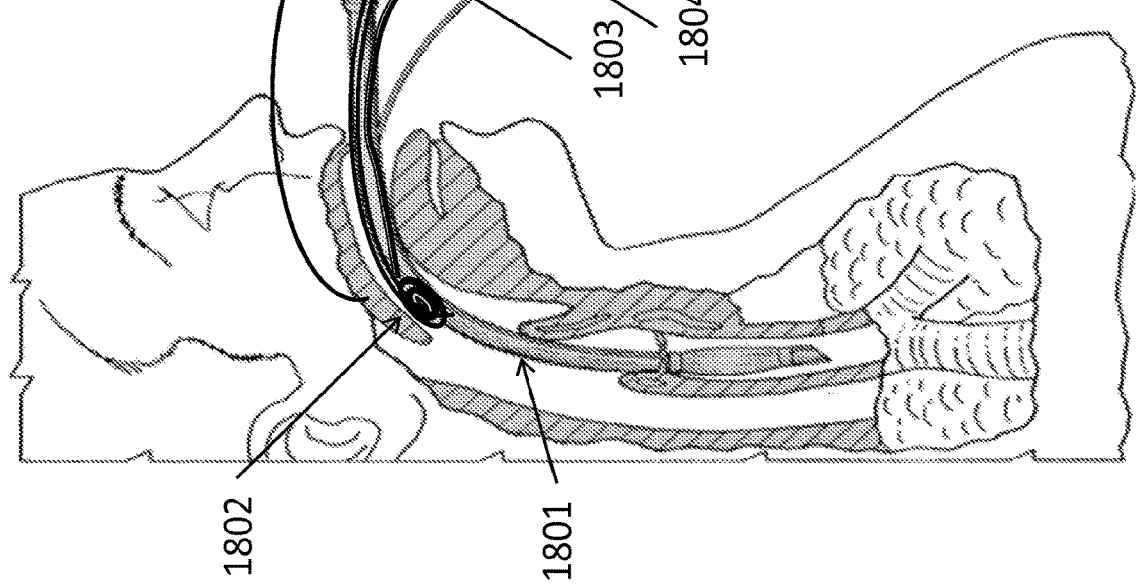
Figure 19B:
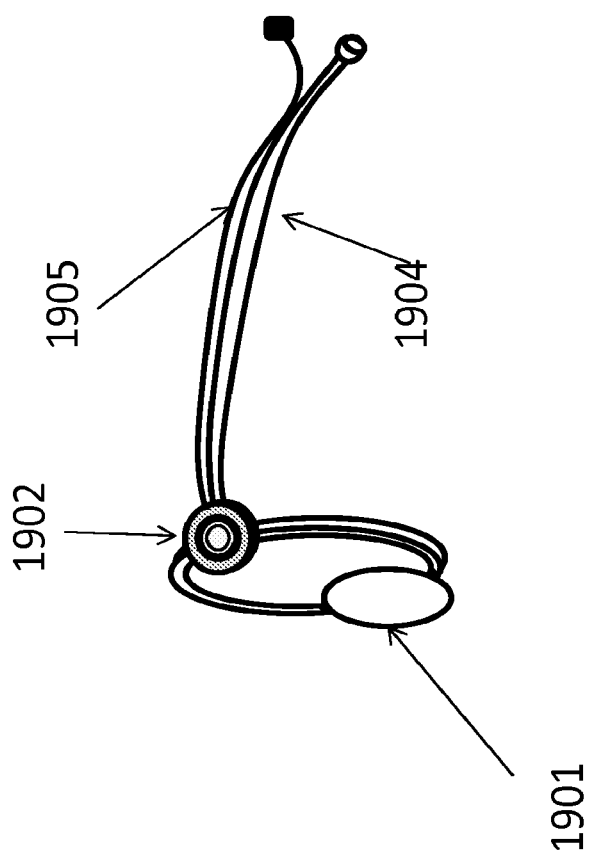
Figure 19A:
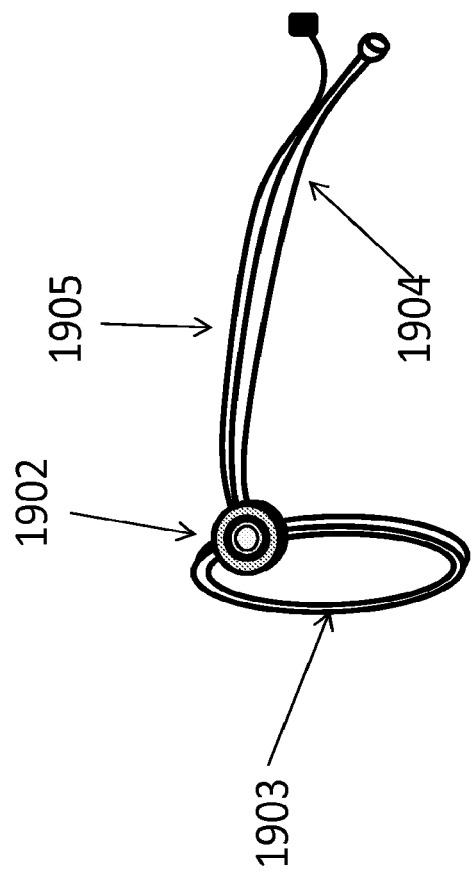
Figure 20B:
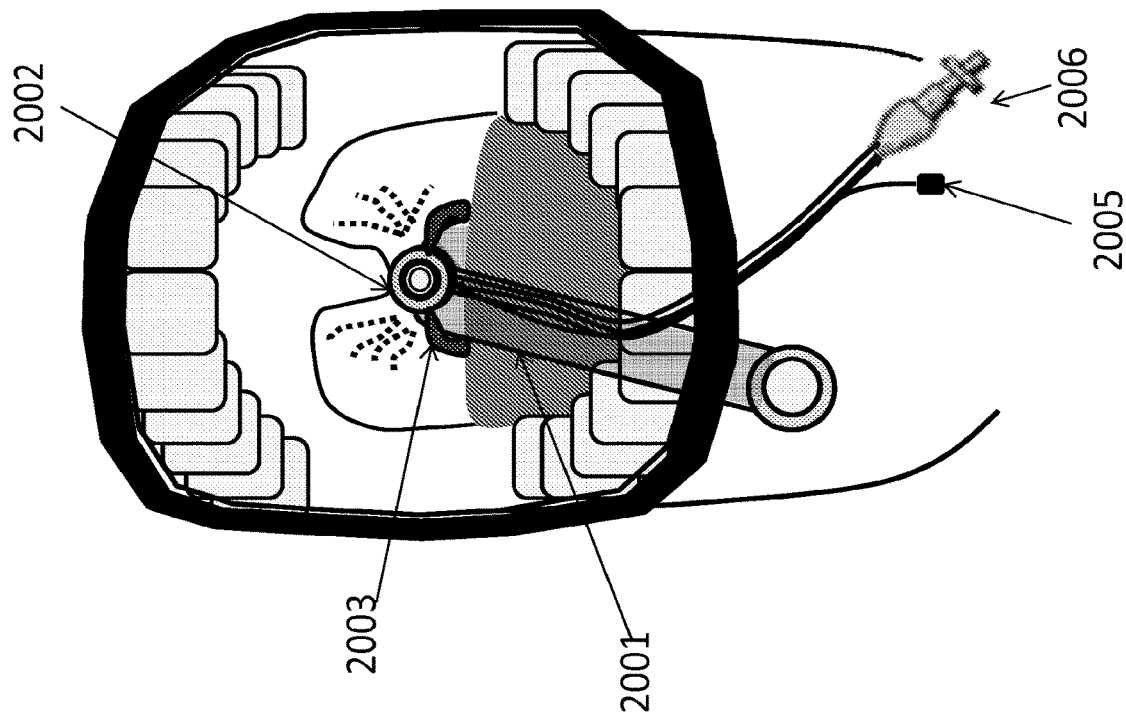
Figure 20A:
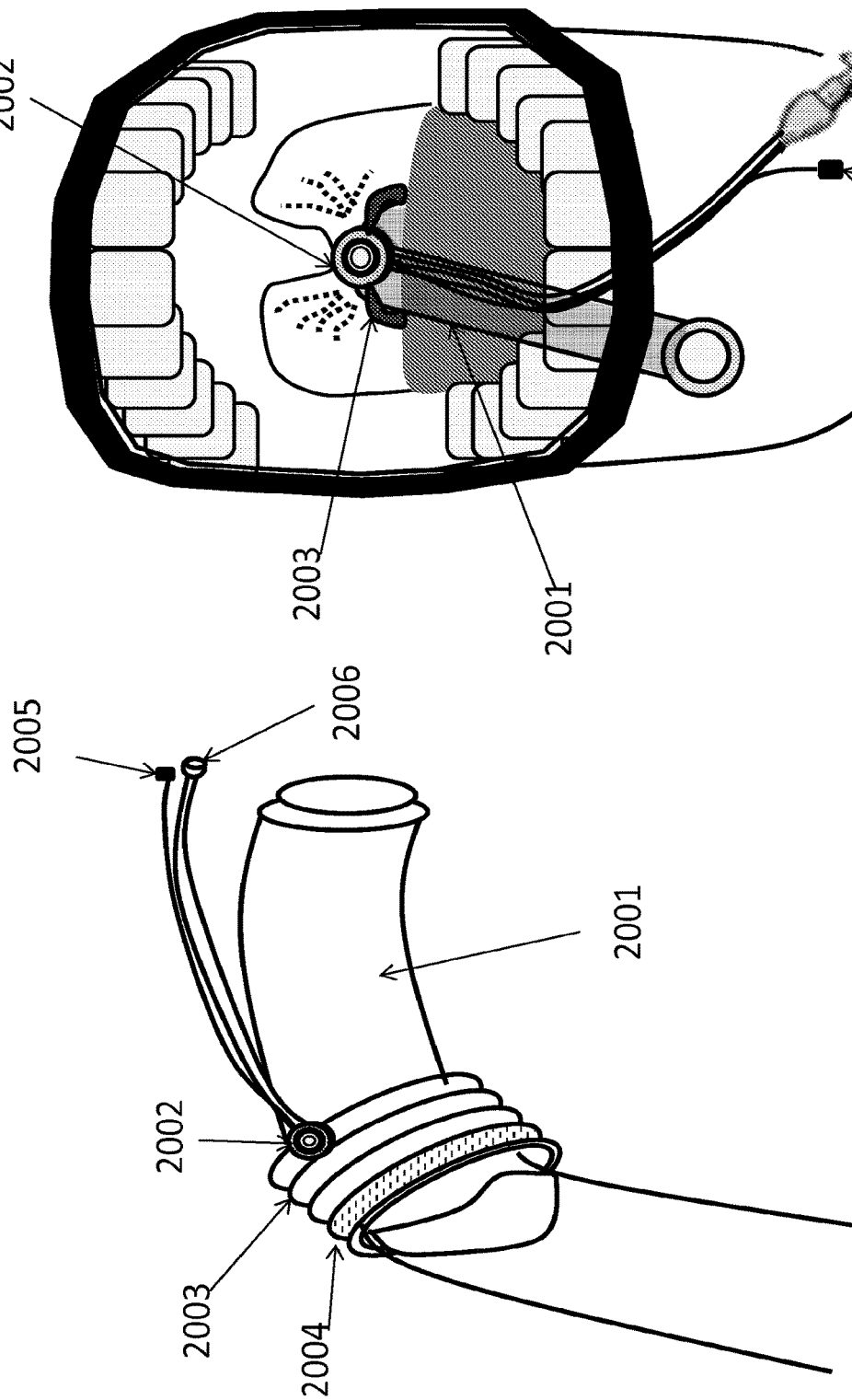
Figure 21:
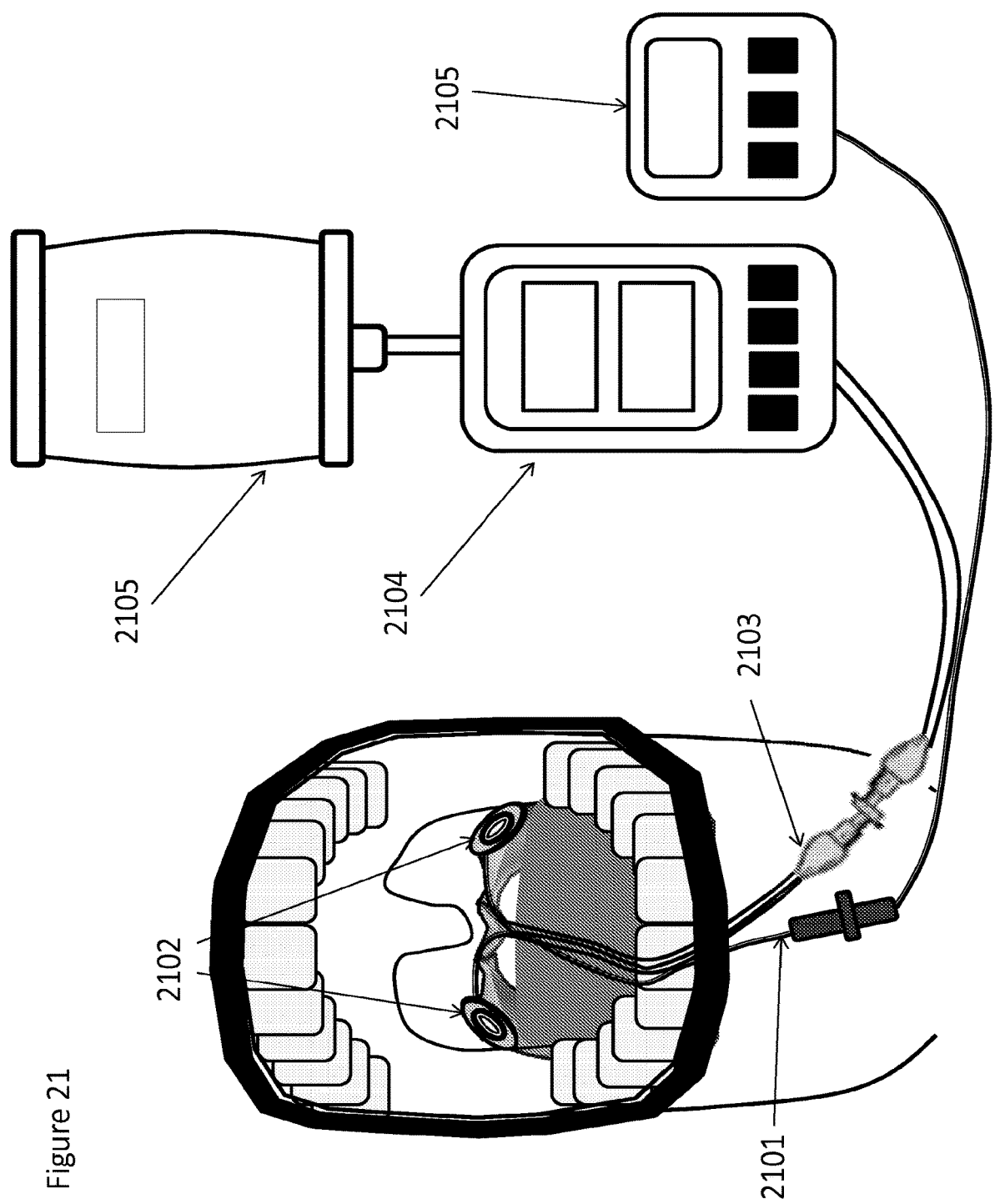
Figure 22A:
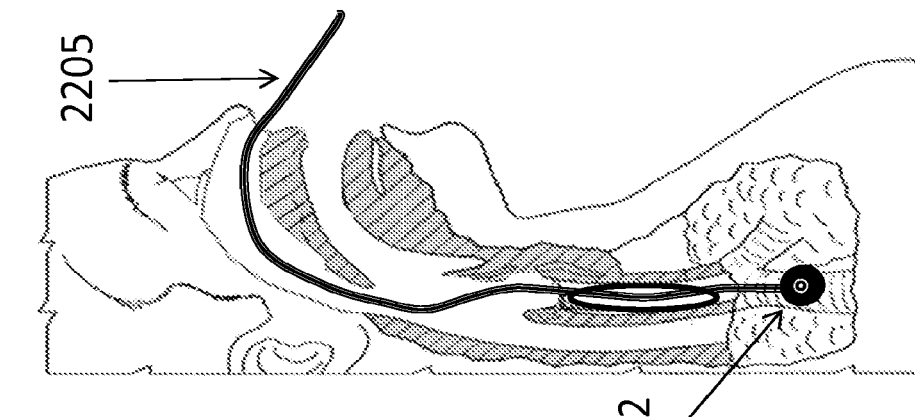
Figure 22B:
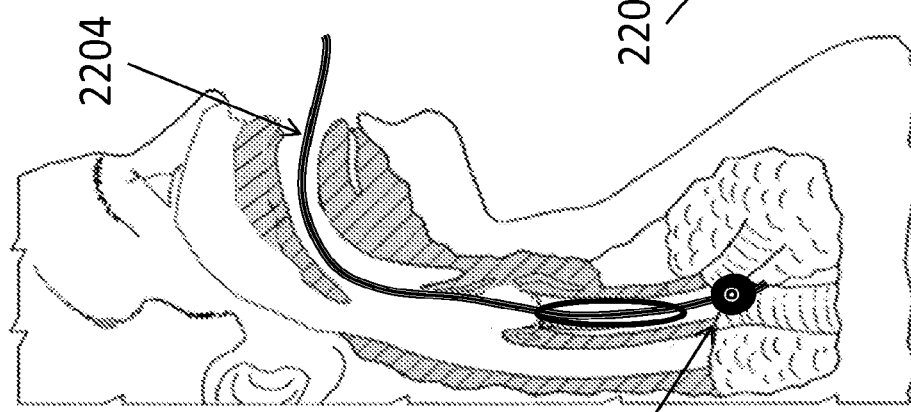
Figure 22C:
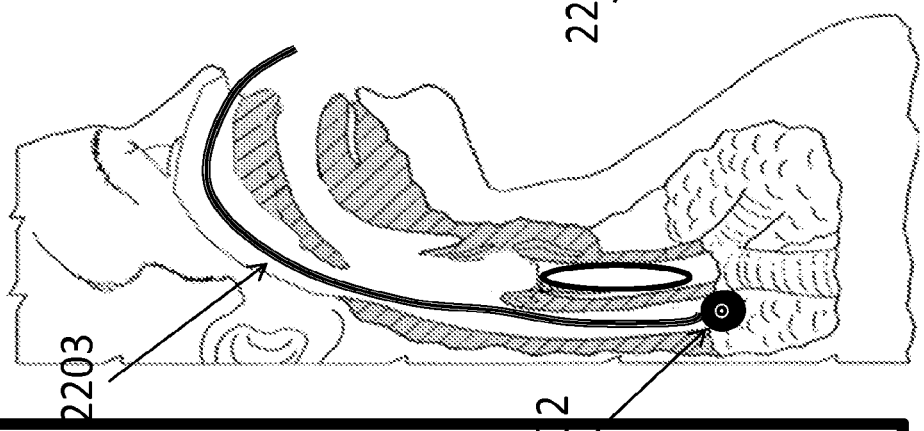
Figure 22D:
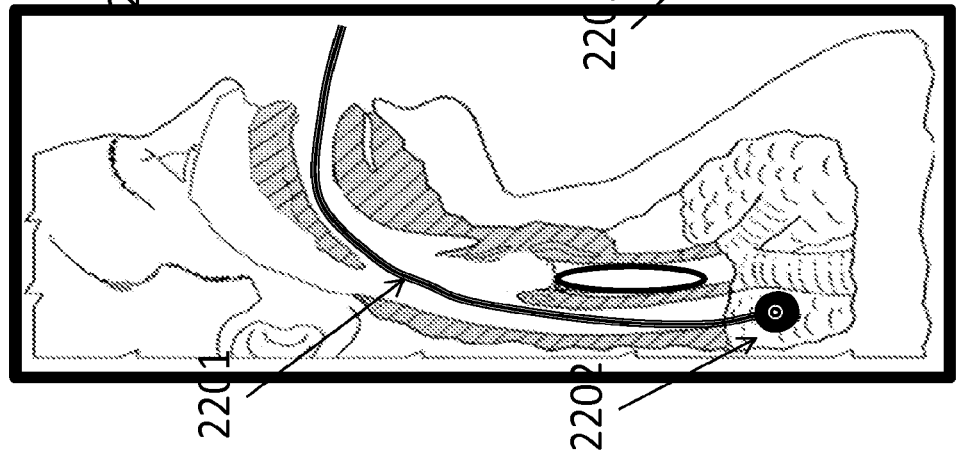
Figure 23:
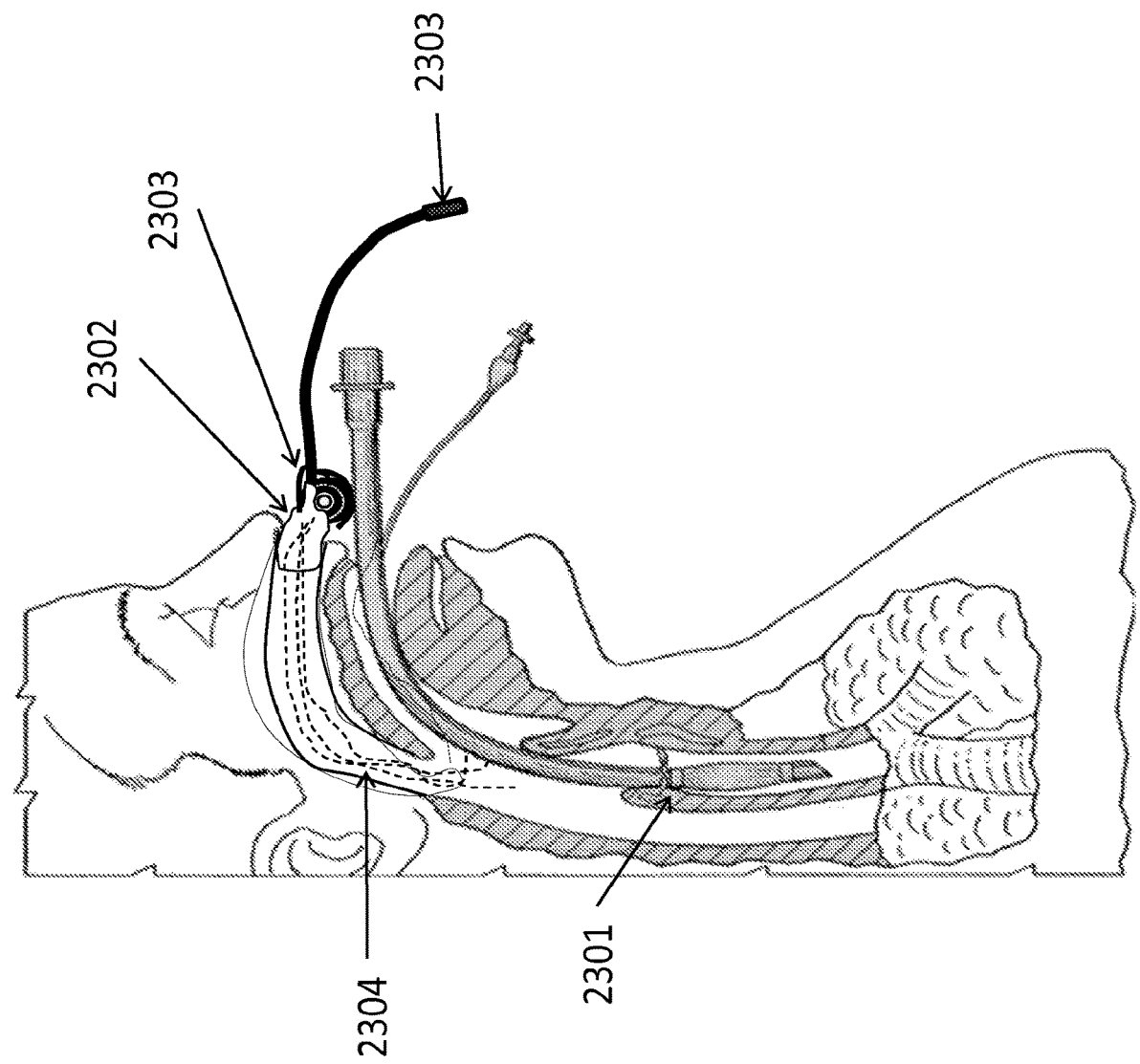

FIGS. 12A-12C are side/perspective views of a device having a flow-splitting valve that has a component that has an unpowered propeller that drives rotation of the component (FIG. 12B) in a fluid flow to allow for flow to oscillate between two flow outlets (FIG. 12C), according to one embodiment;

FIGS. 13A and 13B are perspective views of flow equalization valves, according to two alternative embodiments;

FIG. 14 is a side view of a self-perpetuating peristaltic flow apparatus for multi-lumen flow, such that the flow in alternating lumens drives the alternating peristaltic rollers, according to one embodiment;

FIG. 15 is a cross-sectional view of a device for equalizing flow, such that there are orifice restrictions within the lines of the bifurcated tubes and a filter placed ahead of the orifices in the flow path to prevent the orifices from clogging on particulate matter within the flow pattern ahead of the bifurcation, according to one embodiment;

FIGS. 16A and 16B are bottom and top views, respectively, of an LMA containing a nebulizer for delivery of material to the upper airway, according to one embodiment;

FIG. 17 is a side, cross-sectional view of a patient's head with an LMA placed inside the upper airway, with the LMA containing a nebulizer for delivery of aerosol and/or fluid along the LMA, including but not limited to, at the upper back of the throat, base of the throat, tonsillar pillar, piriform sinus, esophagus, trachea opening, or other area, according to one embodiment;

FIGS. 18A and 18B are side views of an endotracheal tube with a built in nebulizer (in place in the upper airway of a patient in FIG. 18A), for delivery of material to the upper airway, according to one embodiment;

FIGS. 19A and 19B are perspective views of nebulizer connectors that adapt to slid down and/or clip to an endotracheal tube to enable a nebulizer to rest in situ along an endotracheal tube to deliver material to the upper airway or gastrointestinal tract by resting directly within at least a part of the airway, according to one embodiment;

FIGS. 20A and 20B are side and end-on views, respectively (FIG. 20B including a view of a patient's mouth), of a tube adaptor comprising a nebulizer for delivery of substances to the upper airway, such that the tube adaptor with nebulizer can be inserted, clipped to, and/or slid down a endotracheal tube, LMA, or other type of medical tube resting in a body cavity, including but not limited to the upper airway, according to one embodiment;

FIG. 21 is a front view of a system for delivery of nebulized material to the upper airway from one or more nebulizer heads placed inside the airway on a device that can be configured to be inserted in the upper airway, according to one embodiment;

FIGS. 22A-22D are side, cross-sectional views of a patient's head, illustrating several different ways of placing a device with a built in nebulizer in a patient to deliver nebulized materials directly in or adjacent to the area of interest, including but not limited to the upper GI and stomach (FIGS. 22A and 22B) or the lungs and upper airway (FIGS. 22C and 22D), according to various embodiments; and FIG. 23 is a side, cross-sectional view of a patient's head with a device in place in the upper airway that delivers nebulized and/or sprayed material through the nose such that the material floats to the back of the throat to numb the throat.

DETAILED DESCRIPTION

Systems, devices and methods that modulate motor, sensory or autonomic function or perception thereof, are described herein. In some embodiments, the systems, devices and methods may be employed in the airway, the airway being a continuous structure from the nose or mouth to alveolus. The system may also be applied to other areas of the body, including the gastrointestinal tract. The system may be used to reduce sensation, discomfort or pain in a specific area of interest, on a one-time, temporary continuous or long term continuous basis. For instance, the system may be used to reduce discomfort in the upper airway for patients undergoing procedures that require instruments to be placed in or through the upper airway, such as bronchoscopy, laryngoscopy, endotracheal intubation, endoscopy, nasogastric or orogastric tube, laryngeal airway mask ("LMA" or simply "laryngeal mask") or tracheostomy tube, and/or surgical procedures of the upper airway.

Some embodiments include an indwelling piezoelectric nebulizer incorporated within a urinary catheter, balloon catheter, cardiac catheter, abdominal drainage catheter, central venous catheter, or any other medical device resting inside a patient in a fluid medium, air medium, blood medium, or other area for any period of time. In addition, some embodiments may be incorporated into a medical device structure through physical incorporation or secondary attachment. If incorporated into the physical structure, such as within the side of an LMA, the device may be used to deliver material to the upper airway through an external port that allows the material to flow from a source through one or more tubes to one or more outlet applicators on or within the device onto a mucosal surface of the upper airway and/or upper gastrointestinal tract.

In some embodiments, the device may include one or more flow conduits meant to deposit anesthetic medication sourced from one or more reservoirs onto the desired portion of the upper airway, such as but not limited to the tonsillar pillars, tissue near the glossopharyngeal nerve, tissue near the superior laryngeal nerve, mouth, epiglottis, true and false vocal cords, anatomical gutters where saliva flows, and other regions of gag and cough reflex. The flow conduit(s) are connected at their proximal end(s) to one or more proximal reservoirs by one or more connectors and/or tubing, such as but not limited to a press fit, screw threaded, and/or Luer connector. The proximal reservoir(s) contain anesthetic or other medication or substance to be delivered through the device. The flow conduit(s) terminate at their distal end(s) in one or more distal reservoirs, which may also be referred to herein as "applicators" or more generally as areas for applying or delivering a substance to tissue in the patient. The distal reservoirs include some mechanism for allowing a substance to exit the device, such as one or more openings for flow to be expelled onto a sponge or other absorptive or fluid retaining structure and/or through an aerosol or other type of spray nozzle or porous opening to facilitate spray or dripping of material flowing through the conduits to be applied to a desired portion of the airway. Additionally, several flow-splitting, multi-flow single pump tubing systems and/or flow equalization systems may be deployed in the design, between the proximal reservoir(s) and the distal reservoir(s) (or "applicators").

In clinical practice, it is often desirable to have a single lumen connect to the source of anesthetic solution (for example a syringe pump or an IV pump). Within the device embodiments disclosed herein, however, that single fluid source may need to be split among two or more lumens that may each lead to one or more application points for the anesthetic solution.

The disclosed device will modulate sensory, motor or autonomic function in order to, for instance, reduce sensation and discomfort in the airway induced by a foreign object, for instance, an endotracheal tube and/or bronchoscope or endoscope, and/or the sensation associated with mechanical ventilation or a medical procedure being conducted in the airway, respiratory tract or upper gastrointestinal tract.

Reduction or modulation of sensation, discomfort, pain, motor or autonomic function may be achieved through application of the system to a nerve structure (peripheral or central) known to innervate the area of interest. The system may also be directly applied to a specified tissue, so that a desired neuromodulatory or neurosensory effect is achieved. Application to a tissue may also facilitate transit of pharmaceutical compounds through fluid transport in lymphatic vessels, interstitial fluid, and/or blood to nerve structures adjacent to a specified tissue.

Such specified tissues may include but are not limited to the following: nasopharynx, oropharynx, hypopharynx, uvula, epiglottis, tonsils and adenoids, tonsillar pillars, piriform sinuses, false and true vocal cords, larynx, hyoid bone, trachea, bronchi, bronchioles, alveoli, skin, neck, or any mucosal surface in the body including the entire gastrointestinal tract and/or airway. The device and system may be independent or integrated in manufacture with other devices, including but not limited to an endotracheal tube, nasogastric tube, orogastric tube, endotracheal tube securing/anchoring device, bronchoscope, endoscope, transesophageal echocardiography probe, and/or surgical instrument. The system may be applied on a one-time basis, such as to provide local anesthesia to the desired part of the upper airway, intermittently through manual action or the action of built-in pressure relief valve features, or on a continuous basis with syringe and/or infusion pump to provide local anesthetic when instruments rest in situ for prolonged periods of time, such as endotracheal tubes, nasogastric tubes, orogastric tubes, or packing materials in patients admitted to hospital, to the intensive care unit, or who are treated on an outpatient basis. Continuous flow of a substance generally means it is delivered as uniform, oscillatory or pulsatile flow for greater than a few seconds to minutes of time. One-time or intermittent application of a substance generally means it is delivered for less than a few minutes of time.

The system may achieve the desired effect through, but not limited to, delivery of chemicals, drugs, medicines and/or other pharmacological compounds. Medicines known to achieve the desired effect may be employed such as topical anesthetics (e.g., lidocaine, procaine, allocaine, benzocaine, tetracaine, cocaine, eutectic mixture of local anesthetics (EMLA), with or without additive medications such as epinephrine or other vasoactive medications, opiate medications (e.g., fentanyl, sufentanil, remifentanyl, dilaudid, morphine), other sedative medications (e.g. midazolam, propofol, phenobarbital, dexmedetomidine), antimicrobial medications including antibiotics, antivirals, antifungals, bactericidal or bacteriostatic substances. Other medications can also be delivered if an alternate effect is desired (e.g. vasodilator, vasoconstrictor agents, or any other medicine in which direct application to a given area of the body is desired.

The system may be employed on a one-time basis, intermittently, or continuously, ranging from milliseconds to several days or weeks. The device may be left in situ between uses, or removed and reapplied. The device may be anchored to an indwelling device, such as an endotracheal tube, with tape, a clip, or other means, or the device may be not anchored to another indwelling device but may instead be supported by the lateral apposition of the applicators of the device onto the sides of the back of the throat and/or other structures in the mouth or upper airway. The system may be deployed on the skin surface (even if an internal effect is desired locally or at another location), a mucosal surface (even if an internal effect is desired locally or at another location), or via a transvascular, subcutaneous or submucosal needle or microneedle approach.

The system, if applied to a mucosal surface, may be used to deliver anesthetic or other pharmaceutical components to the mucosal surface of the airway or gastrointestinal tract such that nerve structures near, beneath, or adjacent to the mucosal surface are affected by diffusing anesthetic through the mucosal surface into the mucosal tissues and vasculature. The system may be partially or completely disposable or reusable. The system may also be deployed by directly implanting the system around or near the nervous structure or body tissue where the effect is desired.

The system may include a device to deliver the substance to a specific area or nerve using one or more substance delivery reservoirs. "Substance delivery reservoir" is meant to be a broad term, encompassing any suitable applicator, applicator region, sponge, micropore surface, aerosol spray nozzle, nebulizer outlet, delivery conduit, or any other means by which substance can be directed and or applied to a region of interest. In some instances, the terms "reservoir" and "applicator" are used interchangeably in this application. The use of these and other terms indicating means for delivering a substance should not be interpreted as limiting the scope of the device or system.

The substance delivery reservoirs or applicators described herein are capable of applying the substance to the anatomic area of interest in order to achieve the desired effect on the tissue, including nerve tissue. Some embodiments may include one or more needles or microneedles to infiltrate the substance within the tissue. Other embodiments include applicators designed to topically apply the substance to the surface of a tissue. Such applicators may consist of polymers or other materials designed to release a medicine at a desired rate, the substance being impregnated through a chemical bond to the material such that its characteristics of substance release with respect to concentration, dose and time, are known and manipulated to achieve the desired effect. In other embodiments the applicator may be soaked or otherwise partially or fully saturated with the substance, or serve as a reservoir or partial reservoir for the substance, the applicator being manufactured from cotton or other absorbent organic or inorganic material, hydrogels, ionically cross-linked materials and covalently cross-linked materials, polymers such as nylon, polyether ether ketone (PEEK), polyether block amide (PEBAX), polypropylene, polyethylene, poly lactic acid, poly lactic co-glycolic acid, urethane, silicone, polycarbonate, PTFE, silicone, polyurethane, and/or other thermoplastics and/or thermosets. These materials may have characteristics of microporous or macroporous flow channels, open or closed cell sponge structure, and/or laser drilled and/or machine drilled holes that are nano scale, micro scale, millimeter, centimeter, or larger in size.

The above materials may be further coated with a hydrophilic or hydrophobic coating, depending on the desired manner of application in addition to the intrinsic property of the sponge material being used for the applicator. Hydrophilic coatings and hydrophobic coatings may be used to guide the flow and/or affect the resonance time of fluid containing pharmaceutical components such as anesthetics. In addition one or more portions or sides of the applicator sponge may be sealed through the application of a sealant material, coating, or other impermeable or at least partially impermeable structure. Alternatively this seal of one or more portion or sides of the applicator could be accomplished by thermo-welding, heating, and/or melting of the sponge material itself in the desired area to close at least a portion of the flow channels at the outer surface in order to facilitate the greatest amount of application to take place in other areas that were not sealed on the applicator.

The surface contour of the applicator may be manufactured so as to increase the surface area, for example by linear, zigzag, curved or otherwise non-linear structure to serve as retention channels for the substance. Such designs serve the purpose of having a quantity of active substance in direct contact with the mucosal surface such that the resonance time of the substance with the mucosa is sufficient to achieve the desired effect, whether such effect is achieved by diffusion of the substance across the mucosa, through intervening tissue to a nerve structure, such as the glossopharyngeal or superior laryngeal nerves, or directly to the mucosal surface to achieve a topical anesthetic effect. The applicator may be an inflatable balloon which may be perforated, porous in part or in whole.

Structural features of the conduits that the applicators are connected to include one or more flow channels within the conduits, a partial rigidity and/or shape memory, curved structure to facilitate application of the sponge material to the desired anatomical area of the throat, and curved structure to facilitate the retention and stability of the device in situ. These curves in the conduit structure can arch laterally, horizontally, and vertically and/or in multiple dimensions at once in order to transverse the appropriate area such that the application is in the appropriate anatomical area. In the case of the application to the tonsillar pillar region these applicators must curve outward from center and down against the wall of the throat and back on itself to contour around tissue and then back apposed again to the tissue outward to hook or otherwise provide additional retention force against the airway such that the device can be retained. This is in addition the first splay force that is needed for a lateral force pressing the applicators on the lateral sides of the airway.

The applicator(s) may be composed in part or in whole of the above materials, or may use a combination of such materials. The applicators may be divided into sections by insertion of a non-porous layer, so that the active substance reservoir is restricted to certain portion(s) of the applicator, while maintaining an overall shape of the applicator for correct application.

The resonance features of the system that allow for a reservoir of compounds being delivered at the applicator portion include but not limited to sponge types, hydrophobic and hydrophilic channels or features, porous structures, and absorptive materials, and/or capillary action. In systems with two or more applicators that branch or bifurcate from a single or multiple inflowing tubes, these features may serve the added benefit of allowing for somewhat uneven flow from the branched tubing supplying the applicators with compounds but still allow for the applicators to have a relatively even delivery of substance to the desired area such as the mucosa of the airway. This uneven flow may occur as a result of patient's heads moving side to side and/or tilting which creates a height difference at the outlets of the applicators. Additionally, including a resonance feature within the applicator segments will allow for few and/or very tiny inlet holes or pores from the bifurcated tubing segment to the applicator resonance areas. This design feature of small pores on the tubes will allow for pressure head to be built within the system that will facilitate a more equalized and even flow between two or more applicators due to a flow constricted scenario at the tiny flow outlets given the positive pressure head within the system.

Some features of the system may include but are not limited to a corkscrew flow peristaltic valve and/or a flow restrictor or flow splitter valve. Additionally, some embodiments may use a sprayer and/or a nebulizer in order to deliver the material to the site of interest. This may include a nebulizer with a connector to the front of the ET tube for pulmonary lung delivery of nebulized materials through the ET tube and/or out a port in the side of the ET tube ahead of the cuff or in the upper airway. As well the an embodiment may include a nebulizer as a mouthpiece that goes around the ET tube to partially seal the mouth opening for material to essentially just get the area around the airway in the upper part of the mouth or upper airway. Additionally, it may be desired to have a fan with or without a sterilization item like an electrically charged screen, a UV light, and/or an ozone creating mechanism in order to cause material to flow to the desired area and/or sterilize the material and/or the area. Additionally, in one embodiment nose plugs and/or tubing may be used to drive in the nebulized medium through the nose and then around the curve of the airway to hit the sensitive part of the airway. Because the airway is sealed at the lungs by a ET tube or tracheostomy cuff, in this embodiment of delivery of nebulized or sprayed material through the nose plugs the flow of any moving air pushed by the device would be down around the back of the throat and then out the mouth.

The solution containing topical anesthetic may be modified by a substance to alter its pH to alter its efficacy or to target effect to a particular nerve cell or axon type or particular tissue. Such substance may be premixed or added at the point of care through an additional reservoir or pump. pH modulating materials may include but are not limited to sodium bicarbonate, sodium carbonate, sodium hydroxide, potassium hydroxide, hydrochloric acid, sulfuric acid, ammonia, and any other pH modulating reagent known by one skilled in the art. This pH altering effect may increase the therapeutic activity of a pharmaceutical agent like lidocaine by creating a more basic environment that is different from the environment that it is stored in. Additional strategies may include using electrophoresis, ionophoresis, electroporation, or other mechanisms which an electric charge is used to increase the therapeutic activity by modulating pH of a solution containing pharmaceutical compounds and/or creating a gradient and/or pores in tissue that allows for a higher therapeutic activity of the pharmaceutical ingredient. Additionally, electric means to adjust pH including electrolisys and multiple chambers, one for disposal and one for placing back in line for delivery to the body, may be employed to adjust the pH and/or therapeutic activity of the pharmaceutical solution thereof.

A conduit and/or multiple conduits with or without a bifurcation could be used to deliver pharmaceutical components to tissue in the upper airway to achieve numbing, anesthesia, or other desired therapeutic effect. A weep hole, orifice plate, restrictor orifice, restrictor valve, break away valve, pressure relief valve, flow restrictor, and/or any other means to modulate or optimize flow may be used to adjust the flow, such that the device will have built-in operational flow patterns. Those flow patterns could allow the device to operate best in a regime of pressure and flow where a desired therapeutic effect is achieved for a dosage volume. This flow pattern modulated by a flow optimization or restriction valve may serve to restrict too much flow from going through that may cause toxic effects and/or may cause an adverse physical event such as too much fluid in the airway and/or lungs. In the case of a low flow scenario the device may indicate to the operator that a dose below the desired dose is being delivered. In this low flow or in a high flow scenario a noise, or other signal from cavitation, air stream or bubbles, and/or low fluid flow stream through a restricted segment of the conduit may serve to alert the operator that the device is operating outside desired parameters.

In some configurations, the device may have two or more connectors that connect proximally to two or more proximal reservoirs containing the substance to be delivered. Those reservoirs may include, but are not limited to, an IV bag or a syringe. In the case of the IV bag, they would be operable by an infusion pump, and in the case of the syringe, operable by manual actuation or by use of a syringe pump. A syringe pump may be a multi-syringe pump or a single syringe pump. The conduit or conduits used themselves may be divided into multiple flow channels. These flow channels can be built in to a single extrusion or may comprise tubes that are running side by side and held in close proximity by an outer sheath. It may also be advantageous to have an adaptor conduit such that an infusion pump or peristaltic pump would be able to simultaneously drive the movement of fluid through multiple channels in a single conduit. This single conduit would have a single connector to an IV bag or other reservoir. Then the conduit would bifurcate into several flow channels within the conduit that would be placed within the actuation mechanism of the peristaltic infusion pump. The mechanism of the peristaltic pump would drive flow down the conduit and in turn across all if the internal flow channels. The benefit to this would be to equalize the flow, irrespective of pressure, across multiple flow channels from a single reservoir ahead of the pump. In this case the flow channels within the conduit would then bifurcate at the end of the device into the at least two applicators used to apply material into the patient's upper airway or other physiological area. In addition, this single connector, single conduit, multi-channel flow equalizer through the peristaltic pump could then split from the multi-channel into a connector for each channel post the peristaltic pump opposite the single reservoir. These connectors can then be used to connect up to various flow conduits as needed for one or more devices such that the flow could be equalized into device or devices and conduit or conduits downstream of a single reservoir by the action of a peristaltic infusion pump.

In the case of application of pharmaceutical components from the drug delivery conduit to the applicators in the device the system may be made to operate with an off the shelf pump and/or a custom pump. Pressure ranges of operation may, but do not have to be under all conditions, be between 0 to 10 psi from the applied pump pressure. Higher pressures may also be desired. Additionally, in order to achieve safe effects, it may be desired to achieve a flow of less than 20 ml per hour for some toxic compounds. Ideally for lidocaine, a topical anesthetic, a flow between 0.5 ml and 4 ml per hour should be achieved depending on lidocaine concentration between 0.5% and 2% where higher concentrations of lidocaine may demand a lower flow volume. The goal would be to not topically apply more than 1000 mg to the upper airway in a 24 hour period. More application is possible but may necessitate monitoring of blood lidocaine levels in patients. Low concentrations less than 1% lidocaine may be used with higher flow rates than 2 ml per hour so long as they are not flow rates that are too high that the airway becomes flooded. An additional lumen in the conduit or from a separate conduit with a separate connector may be desired at the base of each applicator to connect to a suction tube that would allow for continuous removal of topically infused excess material.

To achieve a flow regime of 2-4 ml per hour of 1% lidocaine, a drug delivery conduit should be between about 0.02" and about 0.15". In some embodiments, the range of diameters may be adjusted, depending on the size of the weep holes at different sections of the drug delivery conduit applicator sections. An ideal internal diameter may be between about 0.02" and about 0.06" for the drug delivery conduit in order to maintain a low pressure drop and also a suitable flow and maximum restricted flow. It may also be desirable for other drug concentrations to have a lower flow that would require an internal diameter between about 0.005" and about 0.035" to achieve flow between about 0.5 ml and about 3 ml per hour. Also, a higher flow rate above about 3 ml and less than about 25 ml may be achieved with non-alarm operating pressure of IV infusion pumps with internal diameters between about 0.03" and about 0.4". Additionally, orifice plates, restriction points, choke points, weep holes, right angles, kinks, and other design features may be included in a conduit (or multiple conduits) to allow for larger tubing diameters but with a series of restrictions that modulate and/or choke flow within optimal operating conditions. It may also be desired to allow for a period of high flow initially to prime the system but then break, or make impossible to re-engage that high flow priming ability once the device is hooked up to the flow pump. This one time priming feature will allow healthcare physicians to prime the device easily with a high amount of fluid while also blocking the device from being inappropriately used if an infusion or syringe pump is incorrectly dialed to a higher flow rate.

A conduit supplies the active substance to part or all of the applicator or reservoir through one or more holes in the conduit. These holes may be on the lateral side adjacent to the airway tissue which to apply the material but need not necessarily be there. Additionally, it may be desired that the exit hole or holes are at the higher point of the applicator, if it is a sponge, such that gravitational forces can help facilitate the movement of fluid down the length of the applicator sponge with only one hole in the conduit per applicator side. There may be a central tubular component serving a distributive rather than reservoir function. Said tubular core may be perforated by virtue of its innate structure, for example, a microporous or macroporous structure, drilled holes or other shapes. Such perforations allow the substance to be delivered to the outer reservoir material along part or all of the applicator to target the desired anatomic areas. This may include an open celled sponge or hydrophilic material that would wick material out of the conduit at a faster rate than it would be passively pumped into the area such that it would serve to help equalize the flow across two conduits connected at a single hub or also facilitate the movement of material out of a conduit and to an application area. The tubular core may be composed of a polyether block amide polymer (PEBAX), polyether ether ketone (PEEK), polytetrafluoroethylene (PTFE), nylon, polyvinylchloride (PVC) or other material, and may consist of a plurality of layers in order to achieve the desired properties of shape, rigidity and biocompatibility.

The system may achieve action on a nerve structure via diffusion of a medication applied to an adjacent mucosal surface through the intervening tissue. Medicines may be directly impregnated onto the applicator although this may be less desirable than continuously or intermittently applying from an external source such as a controlled-rate infusion pump, syringe pump, or balloon pump reservoir. Medicines may be delivered from a reservoir, which may be part of the system or external to the system and is capable of delivering the medicine in a controlled continuous, pulsatile, or bolus fashion. The device may be fitted with pressure-release, duck bill, or other valves to achieve an intermittent effect. A pressure release valve may be connected to the system between the applicators and the pump or reservoir in order to relieve flow and/or block flow in a scenario when the pump is malfunctioning or has been operated incorrectly such that it's flow rate would be unsafe, toxic, and/or cause too much fluid to be delivered to the airway. In addition or separate from this, in order to equalize flow across two or more bifurcations from a single reservoir, orifice plates or other flow restrictor means may be used in conjunction with a pressure regulating valve. In this case a valve may be placed in line of one of the conduit flow areas between a reservoir pump mechanism and the bifurcation serving at least two applicators. The single conduit from the reservoir pump or manual syringe would come to a bladder The applicator(s) may be secured to achieve the desired effect in the desired body area via attachment of another part of the device that is not the applicator to an adjacent structure or foreign body, including but not limited to endotracheal tube, endotracheal tube securing device, bite block, nasogastric tube, orogastric tube, teeth, jaw, natural anatomic ridges, folds orifices or hollows including but not limited to the vallecula, piriform sinuses, tonsillar pillars, tonsils, adenoids, uvula, aryepiglottic folds, false or true vocal cords, hyoid bone, trachea, nasal bone, nasal turbinate, or any part of the airway or gastrointestinal mucosa, and any combination of the aforementioned. In addition the applicators may have contours and curves that facilitate the lodging of the applicators in the correct anatomical position. In addition the curves on the conduit beneath the applicators may curve outward, downward, inward, and then outward, or any combination thereof, such that there is a anchoring effect of force applied to the wall of the airway tissue.

Applicators themselves may comprise sponges but may also be simply spray nozzles or tiny spray ports in the side of the conduit. The system may be attached to anchoring anatomic or foreign body structure via tape, glue or other adhesive, suction, clips, a pre-formed shape which facilitates attachment to a desired structure, a spring loaded, pre-stressed material or balloon of various shapes to apply pressure to keep in place, or a preformed shape which simply sits close to the area of action. The device should have a splay force that is in the shape of a "V" or "Y", such that the opposing forces on the airway tissue cause the device to partially compress such that the spring of the shape causes an application force between the two or more applicators and the wall of tissue. This force is directly opposing and/or this force could also be rotational or lateral in nature by the further outward splay of individual conduits outward after they have made a downward turn from the horizontal to the vertical into the deeper part of the throat. This further outward splay once impacted on a part of the lower part of the airway can cause a rotational effect of force to help anchor the lower part of the system similarly to the horizontally opposing force from the "V" or "Y" shape does to hold the upper part of the device in place against the airway. The system may also be secured to an external body surface using similar methods applied above, even if an internal organ or mucosa surface effect is desired. Multiple attachment points to the body surface may be used. Certain embodiments may utilize a device attaching to both an internal surface, including but not limited to mucosal surfaces, and an external body surface in order to achieve the desired effect. For instance, in order to apply the device to a cranial or other peripheral nerve in the neck, applicators may be optimally positioned internally on the airway mucosa and externally on the skin with the target nerve located between applicators. The device may also comprise a sleeve-like structure for attaching it to a foreign body partially or entirely, including but not limited to an endotracheal tube, nasogastric tube, LMA, orogastric tube, endoscope, bronchoscope, transesophageal echocardiography probe and that sleeve device may serve as an easy insertion mechanism and may also have applicator sections on it.

The system consists of one or more primary central substance delivery conduit(s), which may be connected to a syringe, IV syringe pump, IV pump, syringe, balloon pump, IV bag, or other reservoir. The primary conduit(s) bifurcate(s) into two or more secondary conduits, at a certain angle with respect to each other to achieve the desired anatomic position. The bifurcation may be constructed in such a way as to have certain elasticity to accommodate differences in airway dimensions from individual to individual. This elasticity will spring and/or press outwardly such that direct contact and/or apposition of at least a part of the applicator in appropriate anatomical locations are achieved in the airway, especially with respect to the piriform sinus area and/or the tonsillar pillars. The elasticity and outward springing of a two applicator system will allow each applicator to press on the wall and correspondingly transmit a mechanical force between the two such that it helps equalize the position of the two secondary conduits and/or applicators within the upper airway.

Each secondary conduit is of an appropriate length to horizontally reach the tonsillar pillars. In the region of the tonsillar pillars, each secondary conduit may have a curve or hook shape in order to achieve apposition with the tonsillar pillars on each side. Thereafter, the secondary conduits are curved in a downward direction in order to allow follow the natural anatomic contours to the piriform sinuses. The applicators may be one size fits all and/or may have break away and/or adjustable portions to enable fitting in various types of airway anatomy. In addition the applicators may or may not be configured to touch the base of the piriform sinuses or they may be free floating above the base of the piriform sinus but still in direct contact with the wall of the throat and/or tonsillar pillars. The delivery conduits may in part be inflatable balloons (which could also serve a function as an applicator) in order to account for variations in airway dimensions from individual to individual. Balloons, sponges, or other design features or applicator designs may curve or hook backwards around anatomical features like the tonsillar pillars in order to better hold the device in position from falling forward out of the mouth unless the delivery conduits are compressed together to un hook the applicator portions from the anatomical features of the upper airway.

In order to achieve proper device fit, stability and/or application of anesthetic to appropriate areas, a feature of this design is a distance between the top-most spot of sponge tissue apposition to the bottom most spot of sponge tissue apposition of between 1 cm and 5 cm. This range applies to the distance between the beginning and the end of one continuous sponge as shown in the drawings or to the distance between the first and last of multiple separate sponges. It also applies to any sponge or any other material intended for atraumatic tissue apposition such as fabric, foam, rubber, elastomers, cotton etc. that is in tissue apposition whether it is used for anesthetic delivery or not. An alternate way to define this range is as the distance between the apex of the first inward curve (where the flow port is shown in the drawing) and the end of the arm. In one embodiment, a distance within this range is necessary so that device may appose both the tonsillar pillar region and the piriform sinus region simultaneously. In another embodiment, a distance within this range is necessary so that device may appose the tonsillar pillar region only and have stability that prevents accidental dislodgement during use.

The applicators are at key points to the delivery conduits so as to target key anatomic areas namely the tonsillar pillars, which are anatomically adjacent to the glossopharyngeal nerve, and the piriform sinuses, which are anatomically adjacent to the superior laryngeal nerves. In addition the applicators may only target the tonsillar pillar region but the action of infusing materials into the applicators from a syringe or pump may cause a buildup of material that can then flow down natural anatomic areas of the throat to well and/or be applied in the piriform sinus irrespective of actually having a physical structure of the device in that area. In addition a bolus application effect can be achieved in this manner periodically if the sponge applicators are large enough to maintain a sufficient resonance volume and if that resonance volume is compressed to squeeze out fluid material each time a patient swallows or moves a portion of their tongue or other anatomy. That periodic swallowing and/or squeezing of the sponge applicator causes at least a part of the retained volume of fluid to be expelled out of the applicator and then subsequently fall in a bolus onto the piriform sinus and other lower parts of the esophagus and upper airway anatomy. The applicator-conduit construct may consist of a single, continuous material or of separate components fixed together by heat sealing, glue, adhesive tape, or other adhesive. Multiple applicators may be fixed to each of the secondary conduits, for example, one that targets the piriform sinuses, and another that targets the tonsillar pillars. The applicator may also extend beyond the dimension of the conduits. This could, for example, allow for one-size-fits-all functionality by having a compressible applicator extend beyond the terminus of the secondary conduit. This accounts for variations in the anatomic dimensions of the upper airway by virtue of its compressibility while maintaining contact of the applicator with both the tonsillar pillar and piriform sinus.

The system and/or applicator(s) may be deployed into the appropriate anatomic position in various ways including manipulation manually or with an introducer device under, for instance, direct visualization, direct laryngoscopy, fiberoptic tools to visualize the relevant area. Deployment may also occur by advancing the system and/or applicator(s) along known anatomic structures, including but not limited to the contour of the tongue to the vallecula, nasal passages, or foreign bodies with a known position within the body, including but not limited to an endotracheal tube, nasogastric or orogastric tube. The system and/or applicator(s) may also be placed using inflatable balloon structures, which may or may not have a pre-determined shape when inflated in order to situate the system and/or applicator(s) in the desired position. The deployment process may involve a manipulation in shape of the system or applicator(s) including but not limited to an inflatable balloon, a pre-stressed material assuming a desired shape, such as, but not limited to Nitinol, other metal alloys, polymeric materials and hydrogels, once it is deemed to be in the appropriate position. The aforementioned may be facilitated by an introducer device that allows for placement of the system and/or applicator(s) in the desired location.

In the case of an applicator using a syringe and/or infusion pump, alternative fail safe features may or may not be added. These fail safe features include but are not limited to, a pressure relief valve, a visual cue of unacceptable flow, a flow restrictor plate or choke point, a flow restrictor small segment of tubing to limit the flow, a bypass break away valve, a audible whistle or signal cue, a light activated when bypassed fluid dumps into a secondary holding container, and/or a variety of other means to alert one of improper high flow and/or halt or at least partially divert that unacceptably high flow from reaching the airway.

An exemplary device to reduce the discomfort associated with an endotracheal tube, LMA, bronchoscope or endoscope, consists of a system deployed in order to achieve sensory, nociceptive and reflex are blockade of the glossopharyngeal and superior laryngeal nerves unilaterally or bilaterally, and/or the mucosal surfaces they innervate. The applicator may be applied to the posterior tonsillar pillar and piriform sinuses as the nearest adjacent mucosal surface to the glossopharyngeal and superior laryngeal nerves, respectively. In another instance the system may be additionally applied to the recurrent laryngeal nerves and/or the internal surface of the trachea in order to reduce the discomfort associated with an endotracheal tube balloon, and/or contact with the endotracheal tube itself. Partial or full blockade of the glossopharyngeal and/or superior laryngeal nerves, unilaterally or bilaterally may be done to minimize sensation, nociceptive and reflex arcs associated with contact of the endotracheal tube with the airway or upper gastrointestinal tract. This may lead to a reduction in overall intravenous sedation requirements of patients, especially in patients with endotracheal tubes in the intensive care unit that are being ventilated.

Nebulizers could also comprise applicators in exemplary embodiments of the device. An in-dwelling nebulizer configured to be attached to a medical device may be used in upper airway applications and also in other applications, such as but not limited to within a blood conduit, lymphatic area, bladder, stomach, gastro intestinal system, rectum, mouth, nose, nasal cavities, sinuses, or other areas within the body. Applications can span well beyond numbing of the upper airway to cancer treatment and other drug delivery applications targeted to other areas of the body, especially in the gastrointestinal tract and stomach.

Nebulizer as used within the present document could comprise any manner of nebulizer configurations meant to turn a fluid medium into an aerosol, gaseous liquid, vapor, or similar material comprising a fast flowing small particulate fluid. Various embodiments may pertain to any manner of nebulizing actions, including but not limited to ultrasonic wave nebulizer which may have a piezoelectric element vibrating and creating high-frequency ultrasound waves, to cause vibration and atomization of liquid which may be used in combination with a vaporizer built as a spray nozzle. Nebulizers may also have an electric heating or cooling element such that the fluid nebulized may have a temperature desired for the therapeutic outcome.

Additional types of nebulizers potentially useful for the present applicator embodiments may use an electric vaporizer, either in direct contact with absorbent material in the impregnated atomizer, or in combination with the nebulization technology related to a spraying jet atomizer in which liquid droplets are sprayed out by a high speed air stream that may be configured to pass through venturi injection channels. Nebulizer types may include vibrating mesh nebulizers, jet nebulizers, ultrasonic wave nebulizers, or mechanically or pump activated nebulizers driven through creation of pressure actuation.

Alternative uses beyond as a applicator section in the present embodiment could incorporate a nebulizer into the center section of the flow conduit bifurcation in order to help build pressure at each of the outlets to drive flow through both sides of the bifurcation and help to equalize flow through increasing the pressure.

In using more than one nebulizer there exists the potential for using two or more with a bifurcation so that one controls flow on onside and the other on the other side like a miniature pump in line with the flow conduit. a nebulizer a liquid reservoir chamber supplied by a pump external to the body drives fluid into the nebulizer section. There could also be a float control built into the fluid nebulizer chamber that can detect if the chamber is full to the appropriate level or not (and possibly work between both sides of the chambers with computer algorithms) and then the system would dial up or down the nebulizer activity on one side of the other to push fluid into the outlets of the bifurcations such that flow can be equalized. Additionally this system could shut off flow if desired.

The application of therapeutic material utilizing an indwelling nebulizing mechanism, such as but not limited to a piezoelectric nebulizer, can be done exclusively in the upper airway or in a combination of any of the following, including but not limited to the upper airway, oral cavity, nasal cavity, upper gastrointestinal tract, esophagus, tongue, epiglottis, tonsillar pillars, piriform sinus, behind the vocal cords, in front of the vocal cords, trachea, lungs, and/or stomach. Additionally, other embodiments utilizing an indwelling piezoelectric nebulizing device in the lower gastrointestinal tract, circulatory system, abdominal cavity, or other areas may be useful when connected to other medical devices. As an example, an abdominal fluid drainage tube may be configured to contain an indwelling piezoelectric dispersing device to nebulize fluid into an aerosol or spray form inside the abdominal cavity for delivering medicine inside the abdominal cavity to reduce inflammation, treat or reduce infection, or have another type of therapeutic effect such as delivery for a cancer site such as but not limited to being impregnated into or near a tumor area.

Another proposed system is one in which the flow is split among these lumens equally or in some other ratio. In one embodiment, for example, the one original lumen splits into two lumens where the flow is divided equally among the two lumens. In another embodiment, the one original lumen splits directly into four lumens where the flow is divided equally among the four lumens. In yet another embodiment, the one original lumen first splits into two lumens where the flow is divided equally among them and then each of those splits into two more lumens where the flow is split in a 3:2 ratio.

An embodiment to create a predictable flow split is to reduce the effects of the surface tension of the anesthetic solution utilizing a hydrophilic or hydrophobic coating on the lumens carrying the fluid. A hydrophilic or hydrophobic applicator sponge or wick inside the fluid delivery lumen may also be used.

The low flow velocity conditions necessitated by the low volume of fluid per unit time delivered by the wyshbone device make it difficult to achieve a predictable flow split of the type described above. At low fluid velocity and low pressure head, local effects such as surface tension and elevation differences between exit points dominate and cause fluid to preferentially flow down one lumen or another. Below we describe several ways to address this problem, any of which may be combined to achieve the best results.

In the case of a device associated with a laryngeal mask airway (LMA or "laryngeal mask"), a drug delivery conduit connected to an external reservoir allows for flow of material into portions of the LMA such that these portions or edges would spray or apply physically a liquid material or slurry flowing through the conduit. The objective would be to numb the gag reflex and/or sensation associated with the mucosal surface of the upper airway contacting the LMA by providing a reservoir area within the LMA itself.

In some embodiments the LMA may comprise a hollow structure that can be filled with a liquid drug as a reservoir and then the LMA walls are comprised of a semi-porous material that allows for at least a tiny fraction of material to pass through the wall and affect the tissue on the other side of the reservoir. This material may have a porosity that affects the controlled release rate of the material and/or allows it to be constant, logarithmic, zero order, linear, parabolic, or other types of release profiles of material.

In other embodiments, an LMA could include applicator sections on the sides of the LMA near nerve structures or physical structures of interest to numb. The applicators could comprise sponges and/or aerosol ports on a silicone or rubber material comprising the LMA or separate from the LMA. These applicator openings in the sponges or liquid delivery ports such as but not limited to an aerosol port, allows for material flowing through one or more drug delivery conduits to be applied to the surface of the upper airway and/or upper GI area. There could also then be a dripping or sliding effect of applied material along the surface of the upper airway or upper GI such that the fluid would be applied along an area and/or in multiple areas. This action of sliding or dripping could be in conjunction with salivary flow or could be in conjunction with a guide path provided by surface structures on the LMA or guide structures created by the LMA on native tissue. It is important to note that the application of therapeutic material from the drug delivering LMA can be done exclusively in the upper airway or in a combination of any of the following, including but not limited to the upper airway, oral cavity, nasal cavity, upper gastrointestinal tract, esophagus, tongue, epiglottis, tonsillar pillars, piriform sinus, behind the vocal cords, in front of the vocal cords, trachea, lungs, and/or stomach.

FIG. 1A depicts an exemplary device for the application of topical anesthetic to the upper airway. This device has multiple connectors (101) that connect to one or more proximal drug delivery reservoirs, such as an IV bag or syringe. In this case the two connectors (101) allow fluid to flow into two conduits (102) that are held together inside of a outer casing (103) to help them be at least partially uniform along at least part of the length of the conduits. The outer casing (103) ends before the conduits would enter the mouth (104) and the conduits are held in the correct plane and position by a holder (105). Any part of the conduits (104) or the alignment holder (105) may be used to secure the device, such as to an endotracheal tube with a secondary clip or tape. Once in the mouth or slightly before, the conduits bifurcate laterally into distal conduit portions (106) such that they can apply a uniform outward force on the wall of each side of the airway. Each of the distal conduit portions (106) terminates in an applicator (107) (or "distal reservoir").

FIG. 1B depicts exemplary conduit (106) terminating in an applicator (107) (FIG. 1A) that may include one or more openings (108) to open celled sponges or one or more spray nozzles. In addition to the outward splay of the distal conduit portions (106), the applicator section of the distal conduit portions (106) include multiple curves (109), (110), in order to provide sufficient fixation to the tissue in the upper part of the airway.

FIG. 1C depicts a top view of a lower portion of an exemplary device for applying topical materials, such as topical anesthetic, to the throat. The device comprise two conduits (104) held together (105) and bifurcating horizontally into distal conduit portions (106) to address opposing sides of the airway before diving down into the lower part of the airway near the tonsillar pillars and terminating in an applicator (107) with several orienting curves to help it be retained in the anatomy (110, 111, 112).

FIG. 1D is a perspective view of a portion of a delivery device with conduits (104) that are held together (105), bifurcate (106) to then terminate in applicators (107) and apply material such as a topical anesthetic in the upper part of the back of the throat such as in the tonsillar pillar area.

FIG. 1E depicts an exemplary applicator sponge (109) supplied by a flow conduit (106) that has an applicator hole (108) to wet the sponge (109). The applicator sponge (109) also comprises several curves (110, 111, 113) that enable it to physically contact a side of the airway near the tonsillar pillar area and facilitate the retention of the device in the airway by laterally and rotationally opposing forces from the built in spring forces of the device conduits.

FIG. 1F depicts a rear facing view of an exemplary device with a holder (105) of conduits (106) that supply applicators (107) for delivery of a substance to the upper airway.

FIG. 1G depicts a side view of an exemplary device for applying substances to the upper airway. The device comprises conduits (104) supplying material from a fluid reservoir such as a syringe or infusion bag and a holder (105) to keep the conduits aligned in the correct position. The conduits then splay outward (106) to apply an opposing force to sides of the airway where applicators (107) serve to deliver substances to the throat.

Figure 2:
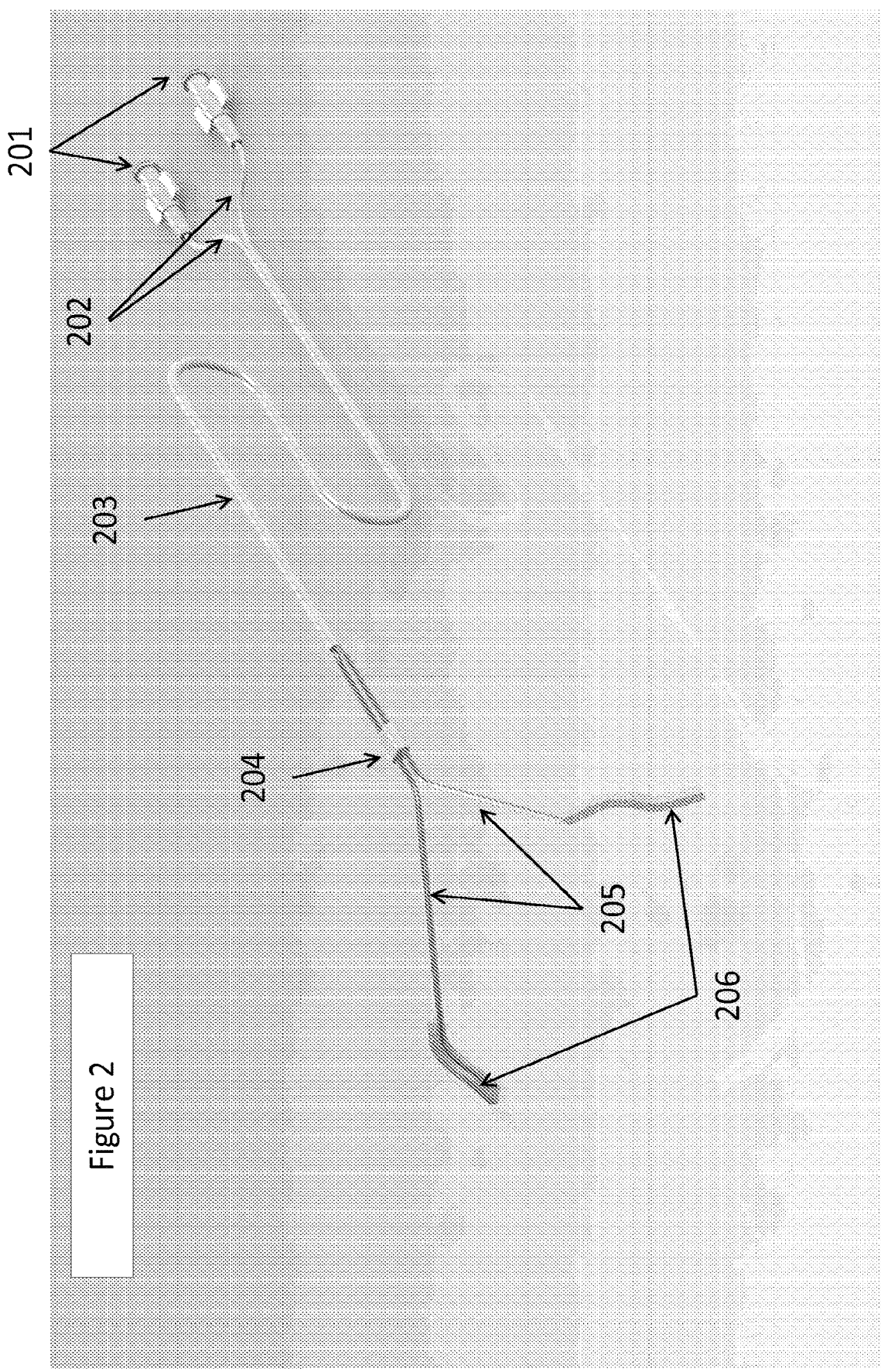
FIG. 2 is a perspective view of device with two connectors, two conduits, and two curved applicators with lateral and horizontal curved design that facilitates application of active substance to the throat and the retention of the device in the desired area of the throat after placement, according to one embodiment.

FIG. 2 depicts a three dimensional rendering of an exemplary device for applying substances to the upper airway. The device includes two connectors (201) to two conduits (202). These connectors (201) attach to material reservoirs such as IV bag or syringe in order to have material to flow through the conduits (202) that are initially held together (203) and fixed into an orientation holder (204) before bifurcating (205) to laterally opposing sides of the back of the upper airway. Then these conduits terminate in sponge applicator sections (206) that apply material to the mucosal surface of the upper airway.

FIG. 3A depicts an exemplary device for applying substances to the upper airway with one connector (301) to one conduit that then bifurcates (302) into two conduits splayed outward (303) that terminate in applicators (304).

FIG. 3B depicts an exemplary device for applying substances to the upper airway with two connectors (305) or one connector (306) to a bifurcated conduit with two tubes (308) or a split lumen (309). The tubing with at least two conduits or two flow channels (307) splays outward to bifurcate (310) and terminate in at least two applicators (311).

Figure 3C:
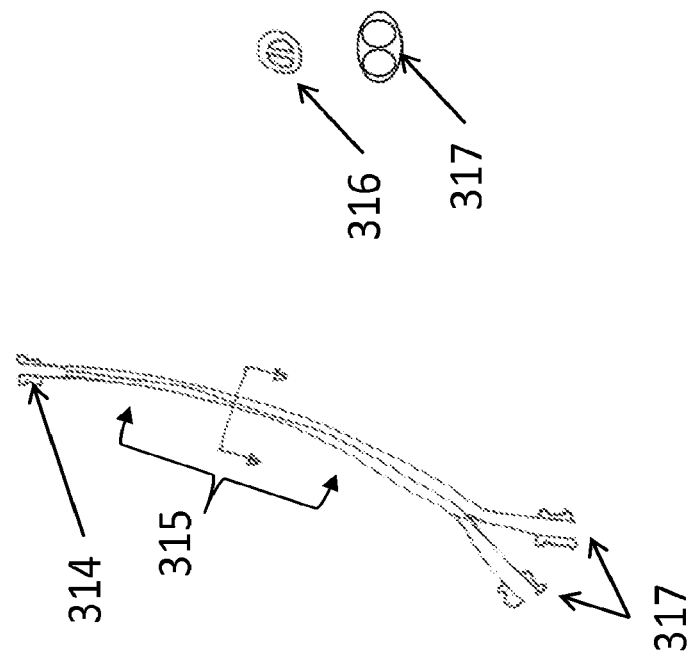

FIG. 3C depicts a portion of an exemplary device with four conduits (312) that terminate in four separate application points (313).

Figure 3D:
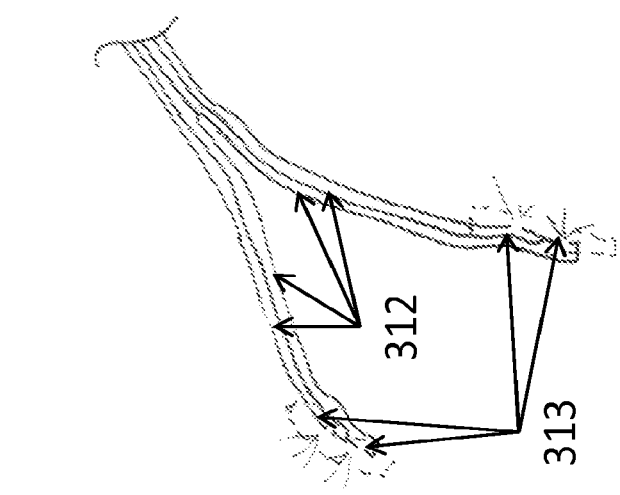

FIG. 3D depicts exemplary adaptor tubing with a single connector (314) to an infusion or drug bag. This single connector bifurcates into at least two flow channels as separate tubes (317) or lumens (316) prior to when it would be pumped in a peristaltic pump. The mid-section pumping portion of the tubing below the bifurcation (315) allows the pump to simultaneously pump each lumen with a single stroke which facilitates a more equal flow out of multiple outlets (317). The outlets can be separate conduits or flow channels that go directly to the device or the outlets can terminate into connectors that can be attached to one or more devices.

Figure 4A:
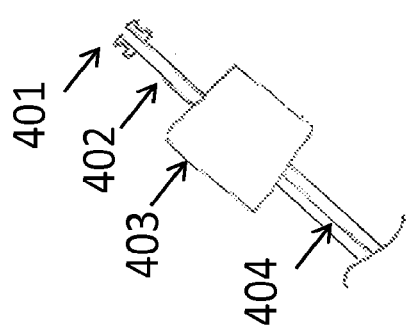
FIGS. 4A and 4B are top views of a device with flow limiting and/or equalization configurations to facilitate a somewhat uniform flow to two different conduits from a single conduit through either a flow equalization and splitter and/or through a pressure relief and/or priming region to create a more pulsatile flow for equalization, according to one embodiment.

FIG. 4A depicts an exemplary flow splitter chamber (403) below a connector (401) to a drug reservoir that has single conduit (402) reaching the flow splitter (403) and then exiting in two or more conduits (404).

Figure 4B:
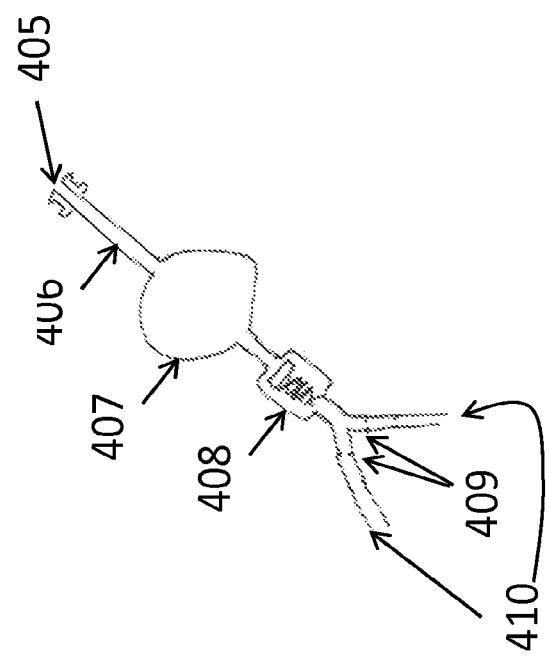

FIG. 4B depicts an exemplary flow equalization mechanism from a single connector (405) to a single conduit (406) to an expansion bladder (407) which may be ridged or spring like expandable and contractible, to a pressure relief valve (408) in line with the conduit. The pressure relief valve (408) is tuned to open above a certain pressure but below the alarm pressure in the pump. The oscillation of the pressure enabled by the pressure relief valve (408) enables flow to be equalized across orifices or small tubes or restrictions (409) and into one or more bifurcations leading to two or more conduits (410).

FIGS. 5A and 5B depict exemplary bottom and top images, respectively, of a LMA (501) comprising a breathing flow tube (503) and outlet (504) for ventilation of the lungs. In this embodiment, a drug delivery device with two applicators (502) is clipped around the outside of the LMA (507) such that the bifurcation (505) of the single or multi lumen tubing is able to direct fluid to the applicators (502) on either side of the upper portion of the LMA near the upper airway. Fluid is delivered to the applicators through a delivery conduit (506) connected to a syringe, infusion bag, pump, or other means to supply fluid meant for delivery to the upper airway by the applicators (502).

FIGS. 6A and 6B depict bottom and top images, respectively, of a LMA (601) configured to contain built-in applicators (602) (or "reservoirs") for delivering fluids to the upper airway via a delivery conduit (606) that is connected to a syringe, pump, infusion bag, or other reservoir containing a fluid. The LMA comprises a breathing tube function with an inlet tube (603) and an opening to deliver air to the lungs (604). The delivery conduit (606) can contain a bifurcation (605) that splits the flow to the applicators (602) through a bifurcation alone, orifice plates, oscillator valve, or other mechanism to drive flow to split from an inlet flow conduit (606) to the outlet applicators (602) delivering to the upper airway.

Figure 7:
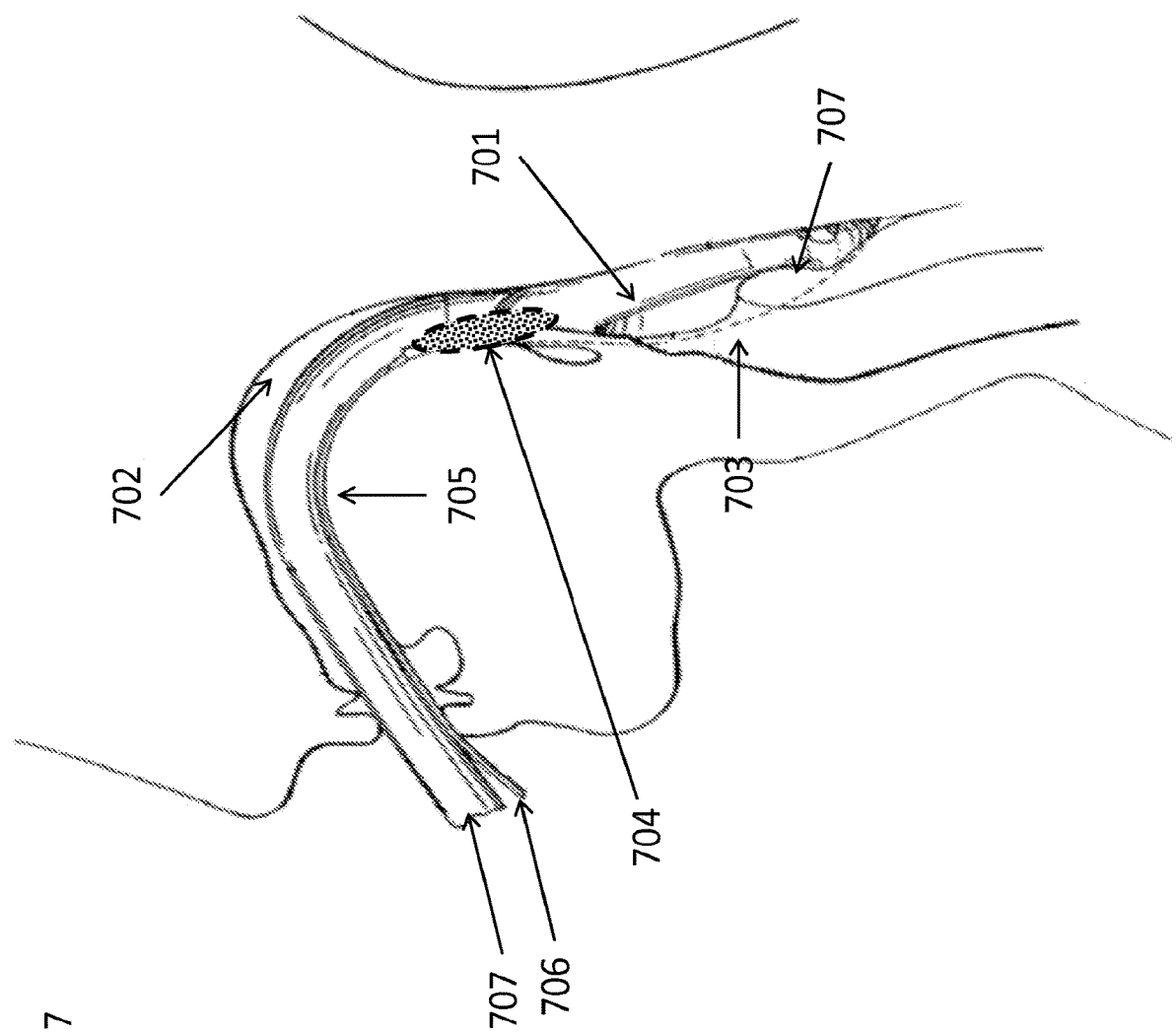
FIG. 7 is a side, cross-sectional view of a patient's head with an LMA in place within the upper airway and a device incorporated into the structure of the LMA to deliver material to the upper airway, according to one embodiment.

FIG. 7 depicts an exemplary side cross sectional view of the upper airway (702) with a LMA (701) inserted. The LMA (701) contains applicators (704) (or "reservoirs") for delivering of a medication to the upper airway external to the lungs. The applicator (704) is supplied with fluid material through a delivery conduit (706) and the lungs are supplied with air through the LMA air tube inlet (707) and exit to the lungs (701) that drives air into the trachea (703). Additionally, a suction port or additional applicators could be placed at the distal section of the LMA (707) if desired. In the case of more than one applicator comprised within the wall of the LMA (701) a bifurcation in the delivery conduit (705) can comprise a flow-splitting valve or orifice or bifurcation to drive flow to multiple applicators at different sections of the LMA (701) to target specific sections of the anatomy in the upper airway and/or upper gastrointestinal tract.

FIGS. 8A and B depict exemplary bottom and top views, respectively, of an LMA (801) containing applicators (802) (or "reservoirs") for delivering material to the upper airway or upper gastrointestinal tract that are connected to a flow conduit (806) through a bifurcation (805). The LMA contains an air inlet (803) from a ventilator and outlet to the lungs (804). Additionally, the applicators are connected past the bifurcation in a conduit loop (807) that further enables pressure equalization within the flow conduit such that the flow is regulated to at least partially equalize between the two applicators (802).

FIGS. 9A and 9B depict exemplary bottom and top views, respectively, of an LMA (901) containing applicators (902) (or "reservoirs") for delivering material to the upper airway or upper gastrointestinal tract that are connected to a flow conduit (906) through a bifurcation (905). The LMA contains an air inlet (803) from a ventilator and outlet to the lungs (904). Additionally, the LMA (901) contains a suction conduit (910) that may be alone or in conjunction to the applicators (902) built into an LMA (901). This suction conduit (910) may be used by healthcare workers or the patient in order to remove fluid at the distal tip (908), side (907), or upper part (909) of the LMA when inserted in situ. This allows for airway secretions and/or delivered fluids to be removed before they advance down the esophagus and/or the trachea. In addition, vomit from the stomach may also be removed this way and/or the applicators may facilitate washing of the throat with simultaneous suction of materials to help reduce aspiration infection risk with the LMA.

FIGS. 10A and 10B depict exemplary bottom and top views, respectively, of an LMA (1001) containing applicators (1002) (or "reservoirs") for delivering material to the upper airway or upper gastrointestinal tract that are each connected to separate flow conduits with separate outlets (1006 and 1005). The LMA contains an air inlet (1003) from a ventilator and outlet to the lungs (1004). Additionally, the flow conduits may be multi or single lumen tubing or connected to each other to allow for a single physical part and a multi flow (1007) to multi reservoir connectors in order to control precisely how much material is delivered to either side of the LMA. Additionally, it should be noted that this device could also have suction ports on either side with multiple suction ports outlets that would function in a similar fashion to the delivery applicators with single conduits connecting to each applicator.

FIGS. 11A-11C depict a flow splitter valve for diverting flow from one conduit (1101) into two conduits (1103), with a rotating splitting component with one opening (1106) and a solid component with two openings (1104). A rotational pin (1105) helps facilitate rotation in a flow stream of the one opening part (1102) using a fin (1107) to drive the movement in a flow.

Figure 12A:
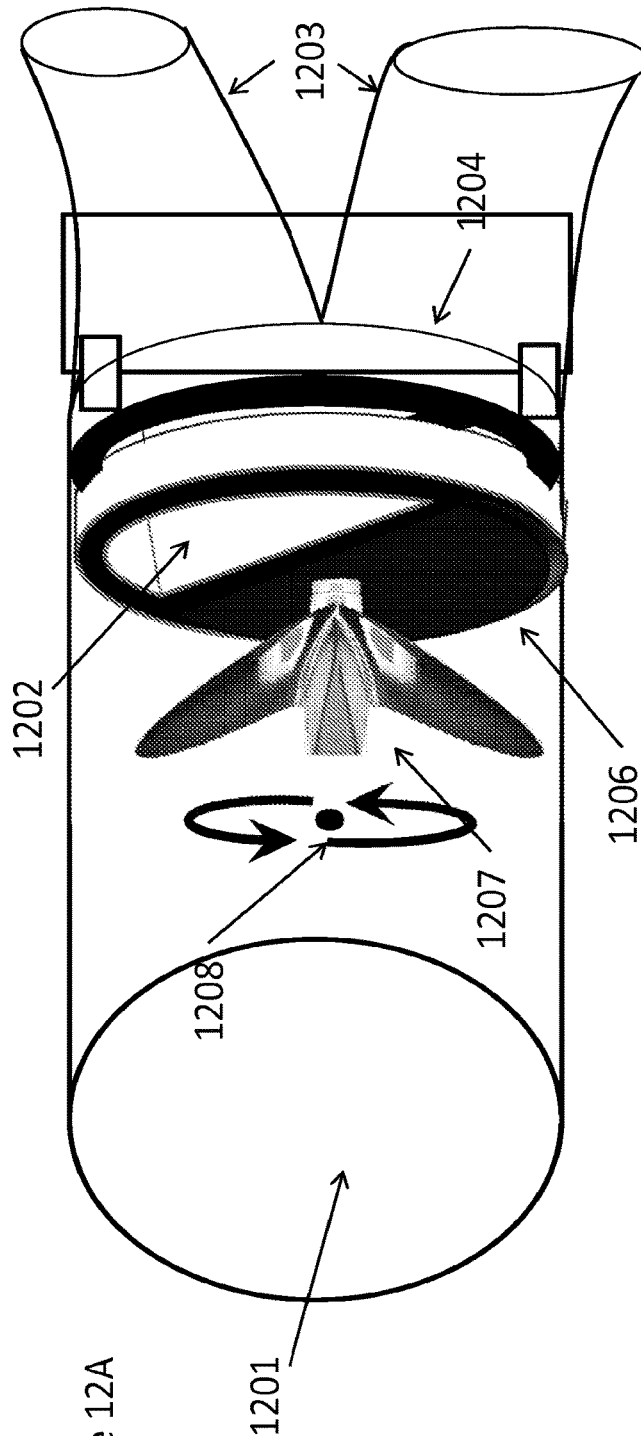
Figure 12C:
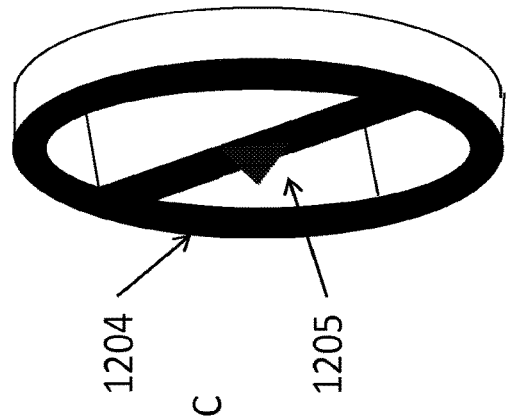
Figure 12B:
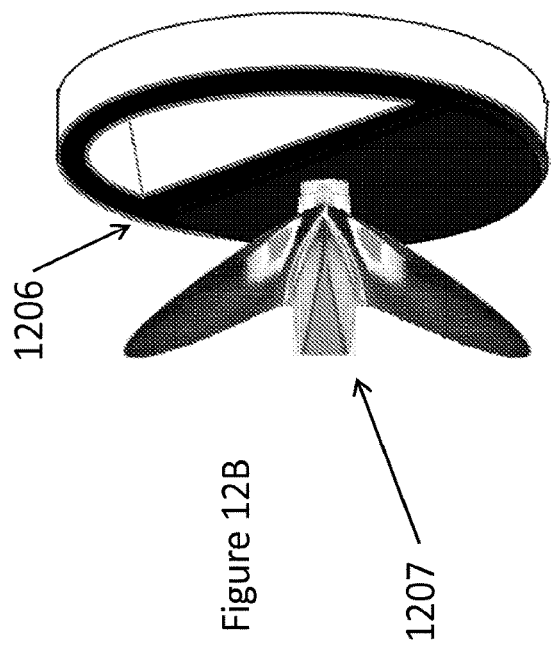

FIGS. 12A-12C depict a flow splitter valve for diverting flow from one conduit (1201) into two conduits (1203), with a rotating splitting component with one opening (1206) and a solid component with two openings (1204). A rotational pin (1205) helps facilitate rotation in a flow stream of the one opening part (1202) using a propeller (1207) to drive the movement in a flow.

FIG. 13A describes a flow splitter valve comprising a single lumen (1301) with a connector for flow input into a splitting manifold (1302) that serves as a reservoir to feed two or more splitting lumens (1303). The size of the diameter of the splitting lumens and the pressure of the flow will determine the extent to which the flow could be split between the two regions in a near equal or equal way depending on the gravitational and frictional effects of the systems in the posterior ends of the multiple splitting lumens (1303).

FIG. 13B describes one way to create a predictable flow split to allow pressure to build up and/or change depending on varying flow in the input channel (1301). This system could also provide for intermittent release, thus creating temporary conditions during which both fluid flow velocity and pressure head are higher. The fluid would then be subject to one or more restrictions (1307) either naturally due to the cross sectional area of the lumens or artificially through an orifice arrangement. In one possible embodiment, the flow splitting equalization effect is achieved by way of a pressure relief valve (1306) and/or an elastic reservoir (1303). The valve opens once pressure has built up in the reservoir and closes either after a volume of fluid has been released through two splitting conduits (1307) such that the pressure in the system drops. This may also close the valve if the flow is turned off to the system through the input conduit (1301).

Figure 14:
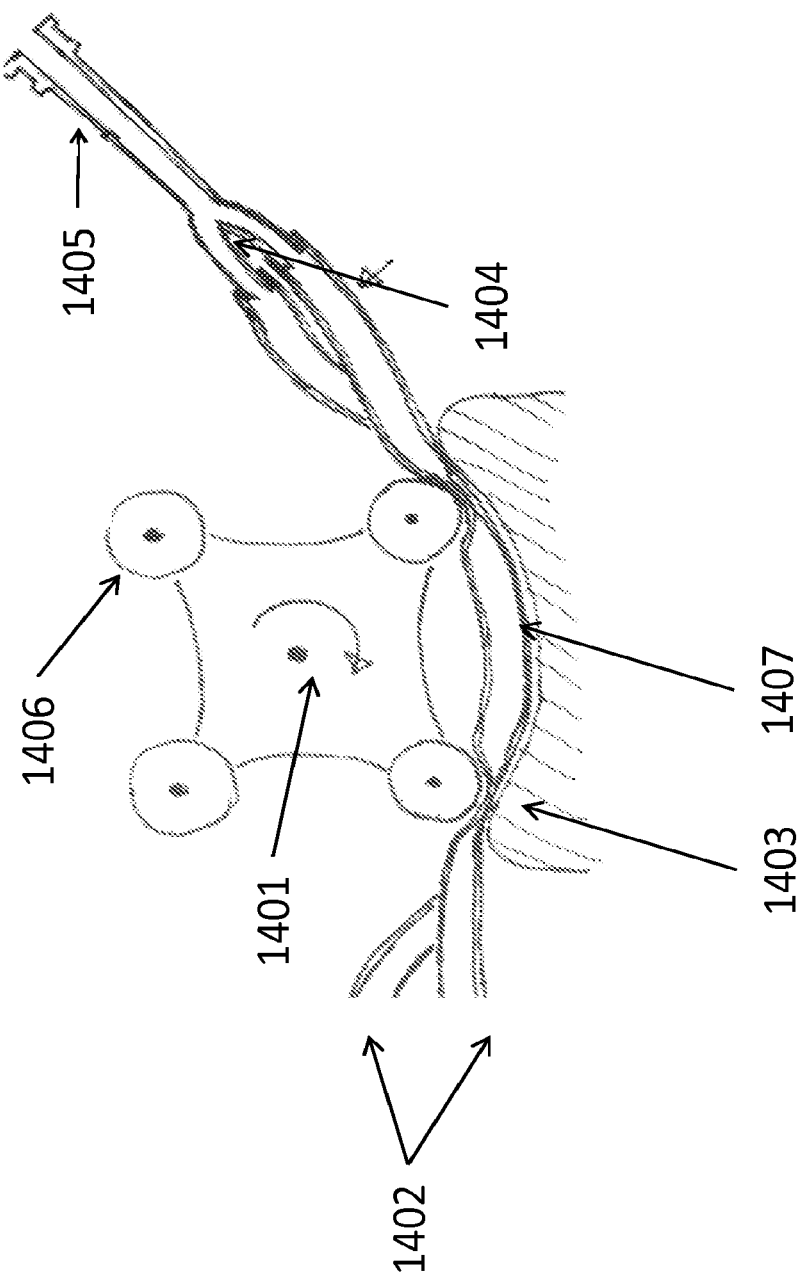

FIG. 14 describes another way to create a predictable flow split by controlling the volume of fluid that flows down multiple lumens (1402) downstream of a flow split (1404) using a freewheeling, unpowered or powered mechanism (1401) similar to those used in positive displacement pumps and/or peristaltic pumps. In one possible embodiment, this mechanism is reminiscent of the working chamber of a peristaltic pump. A source conduit (1405) delivers fluid from a source and to a flow split (1404) where in the tubing after the split (1404) is composed of elastic or flexible tubing (1402) that is placed against a surface (1403) such that rollers or fingers (1406) must compress a portion of the tubing shut and roll or slide along the tubing along with the fluid flow. If the same rollers/fingers or linked or geared rollers/fingers (1406) contact the different lumens (1402), then a fixed ratio of fluid flow can be enforced in all of the different lumens simultaneously due to the multi-simultaneous contact and movement. Multiple conduits (1402) could also be represented by a single multi-lumen tube. In one possible embodiment, the motive force for the movement of this system is provided directly by the pressure head of the anesthetic solution flowing due to gravity through the elastic tubing (1402). In another embodiment the motive force is provided by a separate mechanism such as an electric motor, spring tension, or hydraulic motor. For multi-lumen flow channels the peristaltic activity may be present in two side by side roller mechanisms (1406) that are partially offset as to drive flow in alternating patterns down at least two flow paths such that the force of the flow bulging in the line (1407) is impacting one line when one roller is in contact with a center portion in the highest movable region and a second roller on a second tube is just beginning to contact the tube to begin the flow. This helps facilitate a formation of a seal to be made on offsetting tubing sets with offsetting rollers such that the seal will drive one roller that is coupled to a second roller until a second roller forms a seal which then allows the second roller to drive the first forward and around to seal again and so on.

Figure 15:
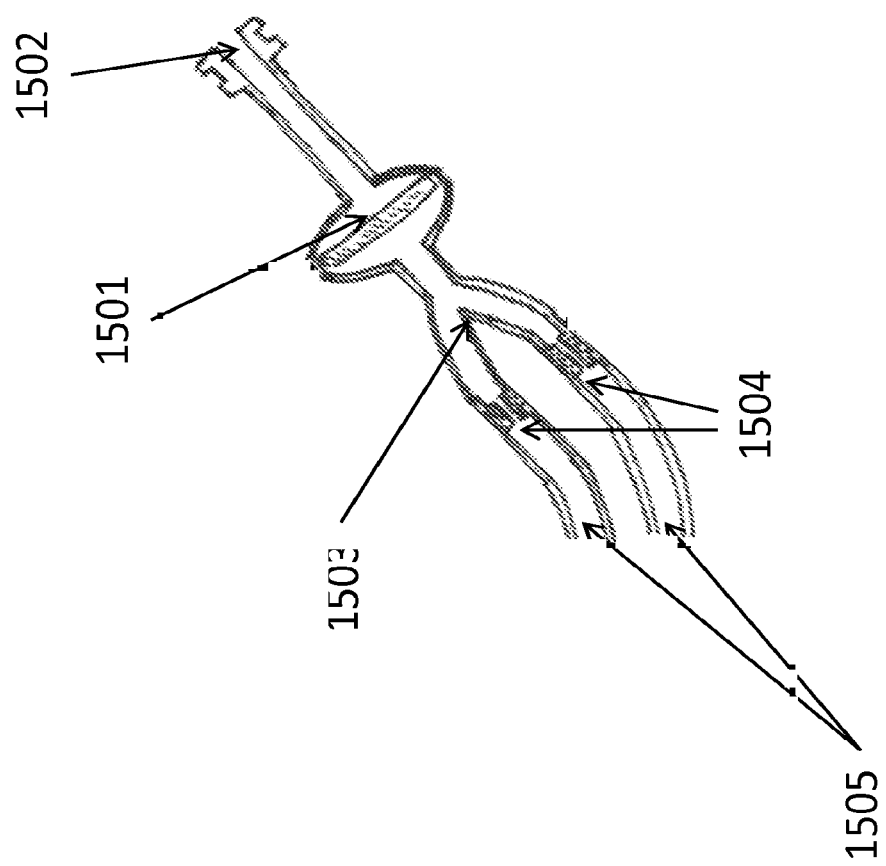

FIG. 15 a third way to create a predictable flow split of a flow fed by a single conduit (1502) is by utilizing flow restrictors (1504) downstream of the split (1503) restrictive enough to create high flow velocity conditions even at the low volumes per unit time delivered by the wyshbone device. These restrictors (1504) may be composed of orifices specifically added to the fluid flow path or be naturally present in the form of the small cross sectional area of the lumens (1505) downstream of the split. The flow restriction (1504) may also be provided together with a filter (1501) or be created by the filter (1501). The filter media (1501) or other material that is water permeable but provides resistance to water flow may be used to create the pressure in the embodiment of a filter based flow restriction (1501). In one possible embodiment, orifices would have a total cross sectional area of between $1.6 \times 10^{-8}$ square inches and $1.6 \times 10^{-6}$ square inches. This may be divided between multiple holes of various shapes and multiple lumens. In another possible embodiment, orifices would be composed of single, circular hole per lumen with a diameter between 0.0001 inches and 0.001 inches. In order to prevent clogging or other changes in the flow characteristics of the flow restrictors in any embodiments a filter may be installed upstream of the flow restrictors. In embodiments where orifices are used, the upstream filter may have a pore size equal to or smaller than the holes of the orifices. (Dimensions are merely exemplary and other dimensions may serve the same purpose.)

Figure 16B:
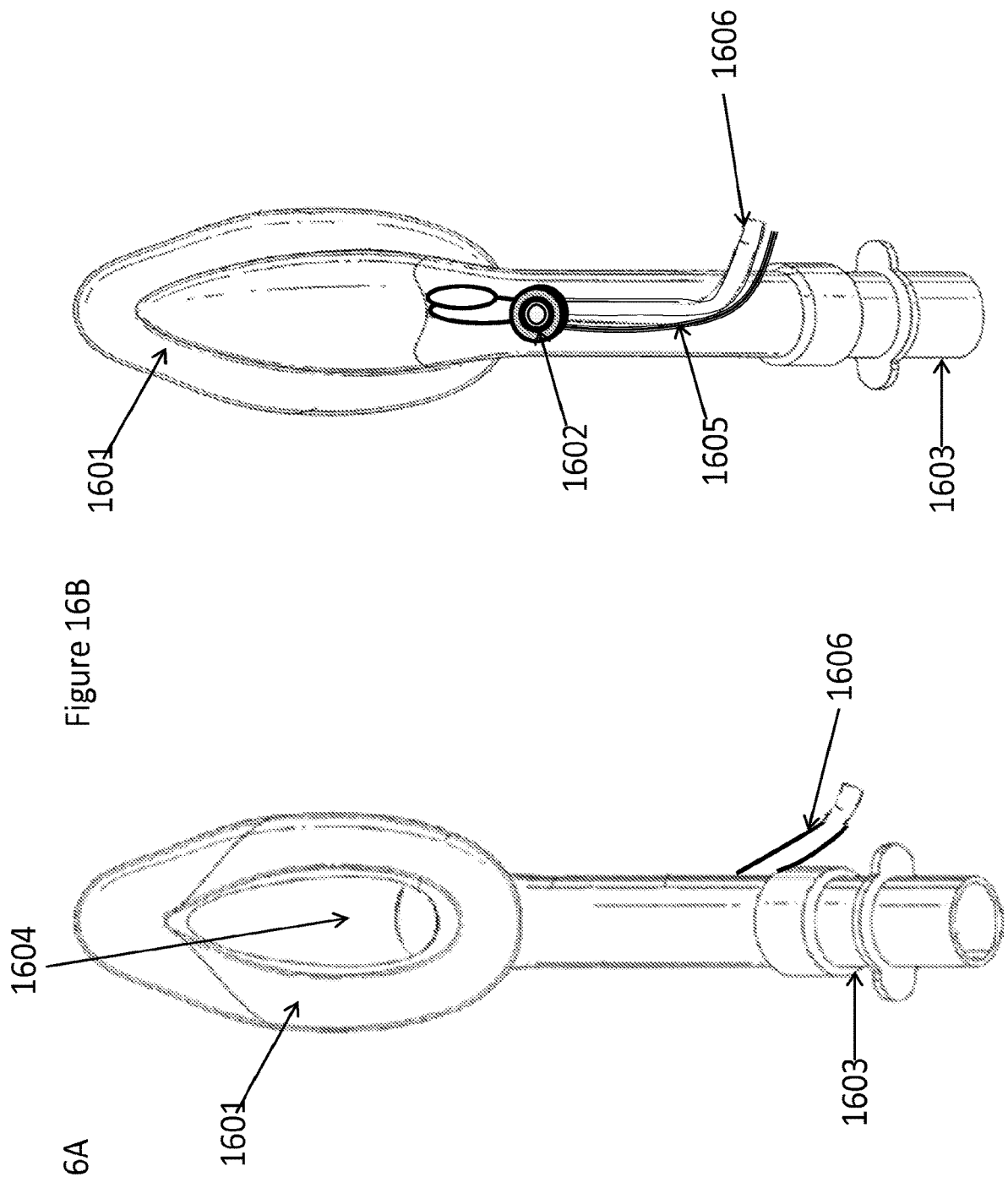
Figure 16A:
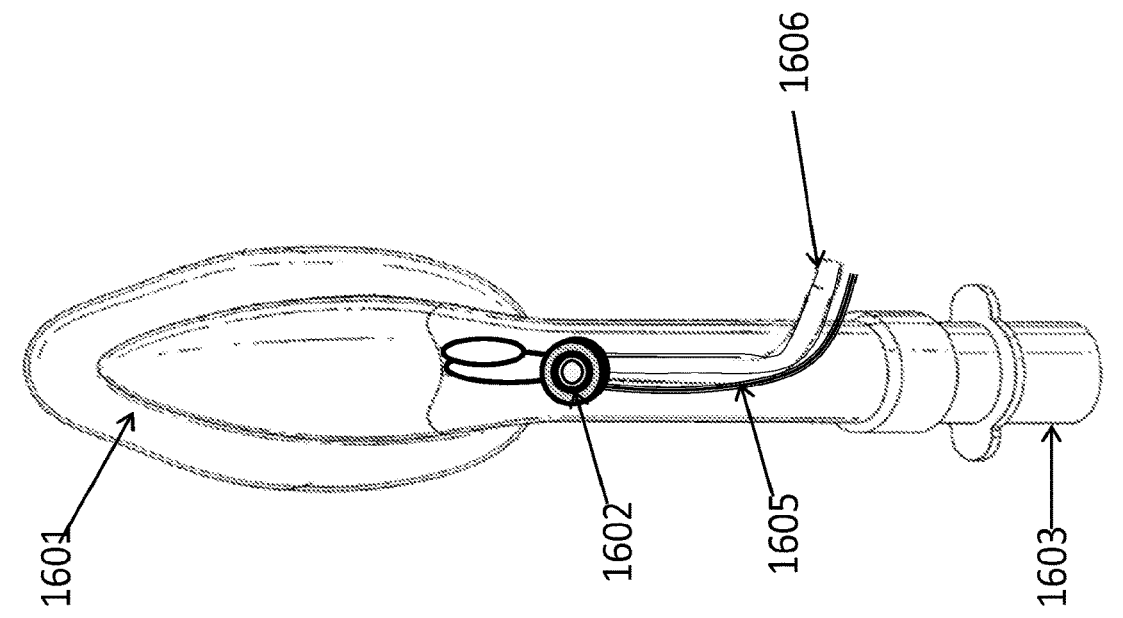

FIGS. 16A and 16B depict bottom and top views, respectively, of an LMA (1601) with an ventilation air inlet (1603) and outlet to the lungs (1604) containing a built in nebulizer outlet (1602) that may or may not contain a powered conduit (1605) to drive a piezoelectric crystal. Alternatively this powered conduit (1605) could contain pressurized air actuation as an alternative to an electric force if a jet nebulizer or pulsed air driven nebulizer is desired through the nebulizer outlet (1602). The delivery of fluid to the head of the nebulizer (1602) is done through a fluid delivery conduit (1606) that is connected to an external reservoir such as but not limited to a syringe, IV bag, fluid pump, or other mechanism of delivering flow.

Figure 17:
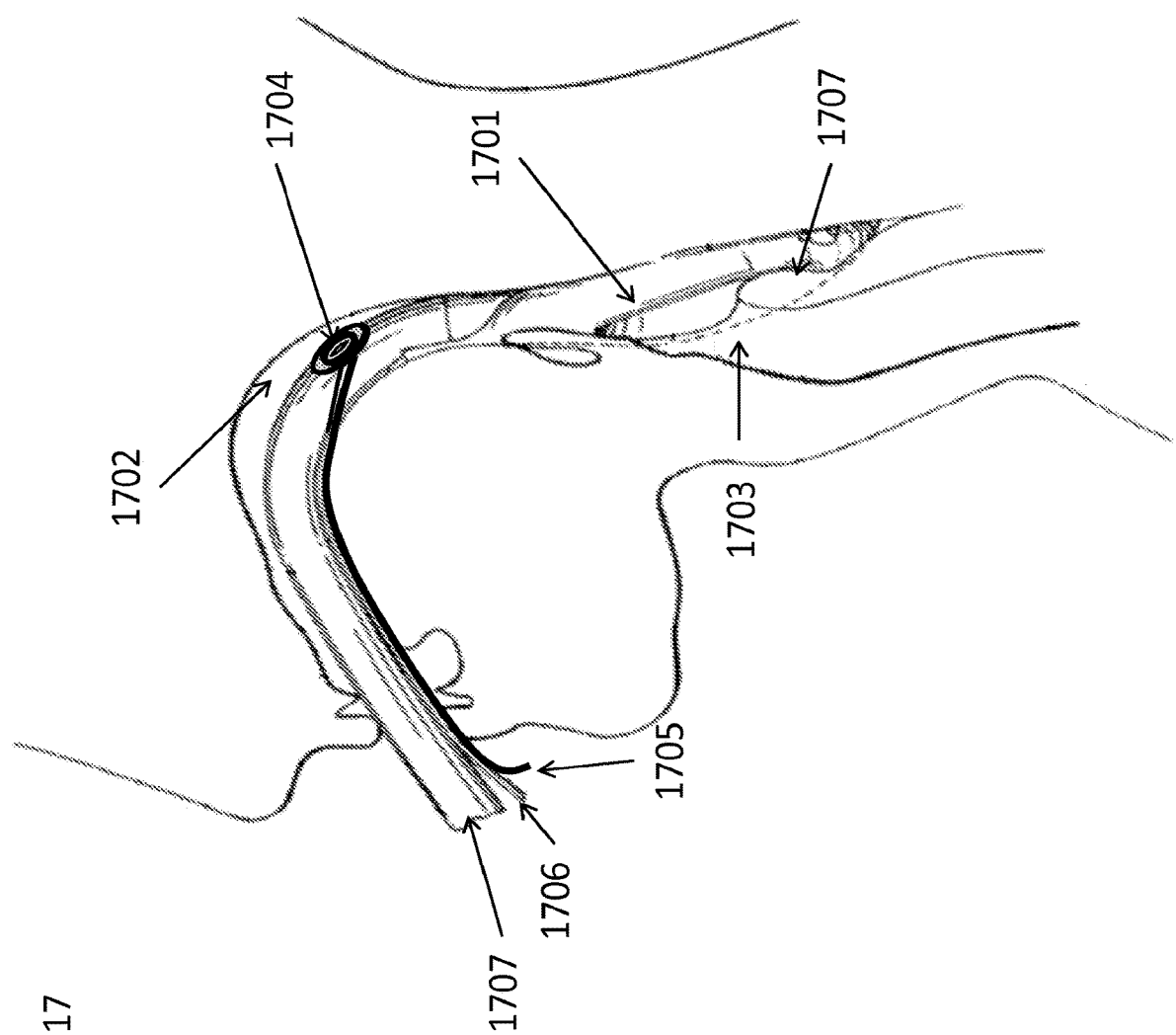

FIG. 17 depicts an exemplary side cross sectional view of a LMA (1701) placed inside an airway (1702) of a patient containing a ventilator air inlet (1707) and outlet to the lungs (1703). Also, this LMA (1701) contains a nebulizer outlet (1704) that rests inside the airway (1702) such that material nebulized into the upper airway and upper gastrointestinal tract is delivered through the combination of a powered conduit (1705) driving actuation of a piezoelectric crystal or pulsatile air actuation and a fluid delivery conduit (1706) connected to an external reservoir. Additionally the delivery nebulizing mechanism and/or a suction port may be placed at different places along the LMA including but not limited to, at the upper back of the throat, base of the throat, tonsillar pillar, piriform sinus, esophagus, trachea opening, or other area.

FIGS. 18A and 18B are exemplary cross-sectional views or a nebulizer applicator (1802) built into a endotracheal tube (1801). The endotracheal tube (1801) with a nebulizer (1802) contains a cuff conduit (1803), nebulizer power driver (1803) that can activate a piezoelectric crystal or drive a pulsatile pressurized airflow, and a fluid delivery conduit (1804) to the nebulizer (1802).

FIGS. 19A and 19B are exemplary views of a nebulizer (1902) configured to click around (1901) or slide down (1903) an medical device such as an LMA, Endotracheal tube, Oral Gastric or Nasal Gastric Tube, or other device such that the nebulizer (1902) would serve as a material applicator by utilizing a powered conduit (1905) to drive the nebulizing action of fluid from a fluid delivery conduit (1904).

FIGS. 20A and 20B are exemplary views of a nebulizer applicator (2002) with a powered conduit (2005) and a delivery conduit (2006) such that the nebulizer (2002) also contains a support guide (2003) and may or may not comprise a sponge section (2004) that can serve as a suction inlet or a secondary reservoir of material absorbed from the delivery by the nebulizer. The nebulizer applicator (2002) can use the support guide (2003) to connect to, or slide down a inserted medical device (2001) such as but not limited to a endotracheal tube, LMA, feeding tube, or other device.

FIG. 21 is a view of a system for delivery of nebulized material to the upper airway utilizing at least one nebulizer applicator(s) (2102) driven by a powered conduit (2101) that can comprise energy for a vaporizer heater, piezoelectric crystal, ultrasonic transducer, air jet, or other mechanism to nebulize fluid delivered through a delivery conduit (2103). The delivery conduit (2103) is supplied through a pump (2104) that draws material from a reservoir (2105). The nebulizer action can be controlled through a control module (2105) that controls the powered conduit (2101) by modulating pressure or energy flow.

FIGS. 22A-22D are side exemplary views of a nebulizer applicator (2202) resting in situ in the lungs, upper airway, lower airway, stomach, or upper gastrointestinal tract. The path to reach these regions can be taken by going transorally (2201 or 2204) or transnasally (2203 or 2205).

FIG. 23 is multiple side views of a nebulizer applicator (2303) through the nasal pathway via nose plugs or nasal delivery guides (2302). The material delivered by the nebulizer (2303) and/or energy to power it is added via a conduit (2303) or series of conduits. The material that is aerosolized and/or nebulized (2304) would be delivered through the nasal conduit to then coat the airway and back of the throat as it settles in the base of the throat due to the blocking cuff of the endotracheal tube (2301).

What is claimed is:

1. A device for delivering a substance to an upper airway of a patient, the device comprising:
   a laryngeal mask airway device, comprising;
      a breathing flow tube configured to extend through the patient's mouth to a distal end configured for placement at or adjacent the patient's larynx;
      a cuff attached to the distal end of the breathing flow tube; and
      an outlet in the cuff for ventilating the lungs;
   a branching conduit that branches from a single proximal end to two separate distal ends that extend in opposing directions along the cuff of the laryngeal mask airway device, wherein the proximal end is configured to couple with a source of the substance residing outside the patient; and
   two substance delivery reservoirs coupled with the laryngeal mask airway device, for delivering the substance to the airway of the patient, wherein each of the two substance delivery reservoirs is attached to a respective one of the two separate distal ends of the branching conduit in two separated locations on the cuff of the laryngeal mask airway device.

2. A device as in claim 1, wherein the two substance delivery reservoirs include multiple micropores through which the substance flows out of the laryngeal mask airway device to contact the airway of the patient.

3. A device as in claim 1, wherein the two substance delivery reservoirs comprise two applicators configured to be located in contact with or near the airway of the patient when the laryngeal mask airway device is disposed in the airway of the patient.

4. A device as in claim 1, wherein a wall of the laryngeal mask airway device is semi-porous, to allow the substance to pass from the two substance delivery reservoirs through the wall of the laryngeal mask airway device.

5. A device as in claim 1, wherein each of the two substance delivery reservoirs is selected from the group consisting of a sponge, a semi-porous balloon, a balloon with micropores, and a cavity formed inside the laryngeal mask airway device.

6. A method for delivering a substance to an upper airway of a patient, the method comprising:
   advancing a laryngeal mask airway device through the patient's mouth and into the upper airway of the patient, wherein the laryngeal mask airway device comprises;
      a breathing flow tube configured to extend through the patient's mouth to a distal end configured for placement at or adjacent the patient's larynx;
      a cuff attached to the distal end of the breathing flow tube; and
      an outlet in the cuff for ventilating the lungs;
      a branching conduit that branches from a single proximal end configured to couple with a source of the substance residing outside the patient to two separate distal ends that extend in opposing directions along the cuff of the laryngeal mask airway device; and
      two substance delivery reservoirs coupled with the laryngeal mask airway device, for delivering the substance to the airway of the patient, wherein each of the two substance delivery reservoirs is attached to a respective one of the two separate distal ends of the branching conduit in two separated locations on the cuff of the laryngeal mask airway device;
   connecting the proximal end of the branching conduit to the source of the sub stance;

allowing the substance to pass from the source through the branching conduit to the two substance delivery reservoirs; and delivering the substance to the airway of the patient by allowing the substance to pass out of the two substance delivery reservoirs.

7. A method as in claim 6, wherein connecting the proximal end comprises connection with a source of an anesthetic substance.

8. A method as in claim 6, wherein delivering the substance comprises allowing the substance to pass through multiple micropores in the two substance delivery reservoirs.

9. A method as in claim 6, wherein delivering the substance comprises allowing the substance to pass through a semi-porous surface of the laryngeal mask airway device.

10. A method as in claim 6, wherein delivering the substance comprises guiding the substance along a surface of the airway of the patient via at least one surface structure on an outer surface of the laryngeal mask airway device.

* * * * *